US007537895B2

(12) United States Patent
Pinkel et al.

(10) Patent No.: US 7,537,895 B2
(45) Date of Patent: *May 26, 2009

(54) COMPARATIVE GENOMIC HYBRIDIZATION

(75) Inventors: Daniel J. Pinkel, Walnut Creek, CA (US); Joe W Gray, San Francisco, CA (US); Anne Kallioniemi, Tampere (FI); Olli-Pekka Kallioniemi, Tampere (FI); Frederic Waldman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/431,094

(22) Filed: May 8, 2006

(65) Prior Publication Data

US 2006/0292608 A1    Dec. 28, 2006

Related U.S. Application Data

(63) Continuation of application No. 11/017,493, filed on Dec. 17, 2004, now Pat. No. 7,238,484, which is a continuation of application No. 09/644,140, filed on Aug. 22, 2000, now abandoned, which is a continuation of application No. 08/903,095, filed on Jul. 30, 1997, now Pat. No. 6,159,685, which is a continuation of application No. 08/468,629, filed on Jun. 6, 1995, now Pat. No. 5,721,098, which is a continuation of application No. 08/166,147, filed on Dec. 14, 1993, now abandoned, which is a continuation of application No. 07/969,948, filed on Oct. 30, 1992, now abandoned, which is a continuation-in-part of application No. 07/846,659, filed on Mar. 4, 1992, now abandoned.

(51) Int. Cl.
C12Q 1/68    (2006.01)
C12Q 1/70    (2006.01)
C12P 19/34   (2006.01)

(52) U.S. Cl. ............... 435/6; 435/5; 435/91.2; 435/91.1; 536/23.1; 536/24.32; 536/24.33

(58) Field of Classification Search .............. 435/4, 435/6, 5, 91.1, 91.2; 536/23.1, 24.32, 24.33
See application file for complete search history.

(56) References Cited

U.S. PATENT DOCUMENTS

| | | | |
|---|---|---|---|
| 4,358,535 A | 11/1982 | Falkow et al. ............. 435/5 |
| 4,647,529 A | 3/1987 | Rodland et al. ............ 435/6 |
| 4,666,828 A | 5/1987 | Gusella et al. | |
| 4,681,840 A | 7/1987 | Stephenson et al. ......... 435/6 |
| 4,683,195 A | 7/1987 | Mullis et al. ............. 435/6 |
| 4,707,440 A | 11/1987 | Stavrianopoulos .......... 435/6 |
| 4,710,465 A | 12/1987 | Weissman et al. ........... 435/6 |
| 4,711,955 A | 12/1987 | Ward et al. .............. 536/25.32 |
| 4,721,669 A | 1/1988 | Barton ..................... 435/6 |
| 4,725,536 A | 2/1988 | Fritsch et al. ............. 435/6 |
| 4,770,992 A | 9/1988 | Van den Engh et al. ...... 435/6 |
| 4,772,691 A | 9/1988 | Herman .................. 536/24.3 |
| 4,888,278 A | 12/1989 | Singer et al. ............. 435/6 |
| 4,981,783 A | 1/1991 | Augenlicht ............... 435/6 |
| 5,085,983 A | 2/1992 | Scanlon .................. 435/6 |
| 5,194,300 A | 3/1993 | Cheung ................ 427/213.31 |
| 5,348,855 A | 9/1994 | Dattagupta et al. ......... 435/6 |
| 5,427,932 A | 6/1995 | Weier et al. ............. 435/91.2 |
| 5,447,841 A | 9/1995 | Gray et al. ............... 435/6 |

(Continued)

FOREIGN PATENT DOCUMENTS

EP    0237362 B1    9/1987

(Continued)

OTHER PUBLICATIONS

Becher et al. Cancer Research, 1983, 43:5010-5016.*

(Continued)

Primary Examiner—Kenneth R. Horlick
Assistant Examiner—Joyce Tung
(74) Attorney, Agent, or Firm—Weaver Austin Villeneuve & Sampson LLP; Emily M. Haliday

(57) ABSTRACT

Disclosed are new methods comprising the use of in situ hybridization to detect abnormal nucleic acid sequence copy numbers in one or more genomes wherein repetitive sequences that bind to multiple loci in a reference chromosome spread are either substantially removed and/or their hybridization signals suppressed. The invention termed Comparative Genomic Hybridization (CGH) provides for methods of determining the relative number of copies of nucleic acid sequences in one or more subject genomes or portions thereof (for example, a tumor cell) as a function of the location of those sequences in a reference genome (for example, a normal human genome). The intensity(ies) of the signals from each labeled subject nucleic acid and/or the differences in the ratios between different signals from the labeled subject nucleic acid sequences are compared to determine the relative copy numbers of the nucleic acid sequences in the one or more subject genomes as a function of position along the reference chromosome spread. Amplifications, duplications and/or deletions in the subject genome(s) can be detected. Also provided is a method of determining the absolute copy numbers of substantially all RNA or DNA sequences in subject cell(s) or cell population(s).

20 Claims, 12 Drawing Sheets
(5 of 12 Drawing Sheet(s) Filed in Color)

U.S. PATENT DOCUMENTS

| | | | | |
|---|---|---|---|---|
| 5,472,842 | A | 12/1995 | Stokke et al. | 435/6 |
| 5,665,549 | A | 9/1997 | Pinkel et al. | 435/6 |
| 5,721,098 | A | 2/1998 | Pinkel et al. | 435/6 |
| 5,800,992 | A | 9/1998 | Fodor et al. | 435/6 |
| 5,830,645 | A | 11/1998 | Pinkel et al. | 435/6 |
| 5,840,484 | A | 11/1998 | Seilhamer et al. | 435/6 |
| 5,856,097 | A * | 1/1999 | Pinkel et al. | 435/6 |
| 5,965,362 | A * | 10/1999 | Pinkel et al. | 435/6 |
| 5,976,790 | A * | 11/1999 | Pinkel et al. | 435/6 |
| 6,159,685 | A | 12/2000 | Pinkel et al. | |
| 6,335,167 | B1 * | 1/2002 | Pinkel et al. | 435/6 |

FOREIGN PATENT DOCUMENTS

| | | |
|---|---|---|
| EP | 0430402 | 6/1991 |
| GB | 2019408 | 10/1979 |
| GB | 2215724 | 9/1989 |
| WO | 87/05027 | 8/1987 |
| WO | 90/05789 | 5/1990 |

OTHER PUBLICATIONS

Trask, Trends in Genetics, 1991, 7(5):149-154.*

Albertson, "Localization of the Ribosomal Genes in *Caenorhabditis elegans* Chromosomes by in situ Hybridization Using Biotin-Labeled Probes," *EMBO J.* 3:6:1227-1234 (1984).

Albertson, "Mapping Muscle Protein Genes by in situ Hybridization Using Biotin-Labeled Probes," *EMBO J.* 4:10:2493-2498 (1985).

Angerer et al., "In Situ Hybridization to Cellular RNAs," *Genetic Engineering: Principles and Methods* Setlow and Hollaender, Eds., Plenum Press, N.Y., 7:43-65 (1985).

Ardeshir et al., "Structure of Amplified DNA in Different Syrian Hamster Cell Lines Resistant to N-(Phosphonacetyl)-L-Aspartate," *Molecular and Cellular Biology* 3:11:2076-2088 (Nov. 1983).

Arnoldus et al., "Detection of the Philadelphia Chromosome in Interphase Nuclei (With 2 Color Plates)," *Cytogenet. Cell Genet.* 54:108-111 (1990).

Bar-Am et al., "Detection of Amplified DNA Sequences in Human Tumor Cell Lines by Fluorescence in situ Hybridization," *Genes, Chromosomes & Cancer* 4:314-320 (1992).

Bayer et al., "The Use of the Avidin-Biotin Complex as a Tool in Molecular Biology," *Methods of Biochemical Analysis* 26:1-45 (1980).

Benton et al., "Screening λgt Recombinant Clones by Hybridization to Single Plaques in situ," *Science* 196:180-182 (1977).

Bergerheim et al., "Deletion Mapping in Human Renal Cell Carcinoma," *Cancer Res.* 49:1390-1396 (Mar. 1989).

Bookstein et al., "Human Retinoblastoma Susceptibility Gene: Genomic Organization and Analysis of Heterozygous Intragenic Deletion Mutants," *PNAS (USA)* 85:2210-2214 (Apr. 1988).

Brigati et al., "Detection of Viral Genomes in Cultured Cells and Paraffin-Embedded Tissue Sections Using Biotin-Labeled Hybridization Probes," *Virology* 126:32-50 (1983).

Brison et al., "General Method for Cloning Amplified DNA by Differential Screening With Genomic Probes," *Molecular and Cellular Biology* 2:5:578-587 (May 1982).

Britten et al., "Analysis of Repeating DNA Sequences by Reassociation," *Methods of Enzymology* 29:363-418 (1974).

Brock et al., "Quantitative in situ Hybridization Reveals Extent of Sequence Homology Between Related DNA Sequence in *Drosphilia melanogaster*," *Chromosoma* 83:159-168 (1981).

Broker et al., "Electron Microscopic Visualization of tRNA Genes with Ferritin-Avidin: Biotin Labels," *Nucleic Acids Research* 5:2:363-384 (1978).

Bufton, et al., "A Highly Polymorphic Locus on Chromosome 16q Revealed by a Probe from a Chromosome-Specific Cosmid Library," *Human Genetics* 74:425-431 (1986).

Bufton et al., "Four Restriction Fragment Length Polymorphisms Revealed by Probes From a Single Cosmid Map to Human Chromosome 19," *Am. J. Hum. Genet.* 38:447-460 (1986).

Buongiorno-Nardelli et al., "Autoradiographic Detection of Molecular Hybrids between RNA and DNA in Tissue Sections," *Nature* 225:946-948 (Mar. 1970).

Burk et al., "Organization and Chromosomal Specificity of Autosomal Homologs of Human Y Chromosome Repeated DNA," *Chromosoma* 92:225-233 (1985).

Buroker et al., "Four Restriction Fragment Length Polymorphisms Revealed By Probes From a Single Cosmid Map to Human Chromosome 12q," *Human Genetics* 72:86-94 (1986).

Cannizzaro et al., "In Situ Hybridization and Translocation Breakpoint Mapping II. Two Unusual t(21;22) Translocations," *Cytogenet. Cell Genet.* 39:173-178 (1985).

Cantor et al. "The Behavior of Biological Macromolecules, Part III," *Biophysical Chemistry*, Freeman & Co. pp. 1183, 1226-1228 (1980).

Cohen et al., "Hereditary Renal-Cell Carcinoma Associated With a Chromosomal Translocation," *N. Engl. J. Med.* 301:11:592-595 (Sep. 1979).

Collins and Weissman, "Directional cloning of DNA fragments at a large distance from an initial probe: A circularization method," *PNAS (USA)* 81:6812-6816 (Nov. 1984).

Connolly et al., "Chemical Synthesis of Oligonucleotides Containing a Free Sulphydryl Group and Subsequent Attachment of Thiol Specific Probes," *Nucleic Acids Research* 13:12:4485-4502 (1985).

Cote et al., "Quantitation of in situ Hybridization of Ribosomal Ribonucleic Acids to Human Diploid Cells," *Chromosoma* 80:349-367 (1980).

Cox et al., "Detection of mRNAs in Sea Urchin Embryos by in situ Hybridization Using Asymmetric RNA Probes," *Developmental Biology* 101:485-502 (1984).

Cremer et al., "Preparative Dual-Beam Sorting of the Human Y Chromosome and In Situ Hybridization of Cloned DNA Probes," *Cytometry* 5:572-579 (1984).

Cremer et al., "Detection of Chromosome Aberrations in the Human Interphase Nucleus by Visualization of Specific Target DNAs with Radioactive and Non-radioactive in situ Hybridization Techniques: Diagnosis of Trisomy 18 with Probe L1.84," *Hum. Genetics* 74:346-352 (1986).

Cremer et al., "Rapid Interphase and Metaphase Assessment of Specific Chromosomal Changes in Neuroectodermal Tumor Cells by In Situ Hybrization With Chemically Modified DNA Probes," *Exp. Cell Res.* 176:199-220 (1988)

Cremer, T. et al., "Detection of Chromosome Aberrations in Metaphase and Interphase Tumor Cells by In Situ Hybridization Using Chromosome-specific Library Probes," *Human Genetics* 80:235-246 (1988).

Cremer, T. et al., "Rapid Metaphase and Interphase Detection of Radiation-Induced Chromosome Aberrations in Human Lymphocytes by Chromosomal Suppression In Situ Hybridization," *Cytometry* 11:110-118 (1990).

Davies, "The Application of DNA Recombinant Technology to the Analysis of the Human Genome and Genetic Disease," *Human Genetics* 58:351-357 (1981).

Dennis et al., "Cytogenetics of the Parthenogenetic Grasshopper *Warramaba virgo* and its Bisexual Relatives," *Chromosoma* 82:453-469 (1981).

Devilee et al., "Detection of Chromosome Aneuploidy in Interphase Nuclei from Human Primary Breast Tumors Using Chromosome-Specific Repetitive DNA Probes," *Cancer Res.* 48:5825-5830 (Oct. 1988).

Drmanac, R. et al., "Sequencing of Megabase Plus DNA by Hybridization: Theory of the Method," *Genomics* 4:114-128 (1989).

Drumam et al., "Detection of Species Specific Chromosomes in Somatic Cell Hybrids," *Som. Cell. Molec. Genetics* 11:6:571-577 (1985).

Erikson et al., "Heterogeneity of Chromosome 22 Breakpoint in Philadelphia-positive (Ph+) Acute Lymphocytic Leukemia," *PNAS, USA* 83:1807-1811 (Mar. 1986).

Fisher et al., "Adhesive and Degradative Properties of Human Placental Cytotrophoblast Cells In Vitro," *J. Cell Biol.* 109:2:891-902 (1989).

Fisher et al., "Molecular Hybridization Under Conditions of High Stringency Permits Cloned DNA Segments Containing Reiterated DNA Sequences to be Assigned to Specific Chromosomal Locations," *PNAS, USA* 81:520-524 (Jan. 1984).

Friend et al., "A Human DNA Segment With Properties of the Gene that Predisposes to Retinoblastoma and Osteosarcoma," *Nature* 323:643-646 (Oct. 16, 1986).

Fuscoe et al., "An Efficient Method for Selecting Unique-Sequence Clones from DNA Libraries and Its Application to Fluorescent Staining of Human Chromosome 21 Using in situ Hybridization," *Genomics* 5:100-109 (1989).

Fuscoe et al., "Construction of Fifteen Human Chromosome-Specific DNA Libraries from Flow-Purified Chromosomes," *Cytogenetic Cell Genetics* 43:79-86 (1986).

Gall et al., "Formation and Detection of RNA-DNA Hybrid Molecules in Cytological Preparations," *PNAS, USA* 63:378-383 (1969).

Gall et al., "Nucleic Acid Hybridization in Biological Preparations," *Methods in Enzymology* 21:470-480 (1981).

Gerhard et al., "Localization of a Unique Gene By Direct Hybridization in situ," *PNAS* 78:3755-3759 (1981).

Gray et al., "Flow Cytometric Detection of Chromosome Aberrations," (Abstract) Conference on Flow Cytometry in Cell Biology and Genetics, Clift Hotel, San Francisco, California, Jan. 15, 1985-Jan. 17, 1985.

Gray et al., "Fluorescence Hybridization to Human Chromosome 21 Using Probes From A Charon 21 A Library," *Cytometry* (Supp. 1) Abst. 19: p. 4 (1987).

Gray et al., "Molecular Cytogenetics, Diagnosis and Prognostic Assessment," *Current Opinion in Biotechnology* 3:623-631 (1992).

Grunstein et al., "Colony Hybridization: A Method for the Isolation of Cloned DNAs That Contain A Specific Gene," *PNAS, USA* 72:10:3961-3965 (Oct. 1975).

Haase et al., "Detection of Two Viral Genomes in Single Cells By Double-Label Hybridization in situ and Color Microradioautography," *Science* 227:189-192 (1985).

Harper et al., "Localization of Single Copy DNA Sequences on G-Banded Human Chromosomes by in situ Hybridization," *Chromosoma (Berl.)* 83:431-439 (1981).

Harper et al., "Localization of the Human Isulin Gene to the Distal End of the Short Arm of Chromosome 11," *PNAS, USA* 78:7:4458-4460 (Jul. 1981).

Henderson, "Cytological Hybridization to Mammalian Chromosomes," *International Review of Cytology* 76:1-46 (1982).

Herzenberg et al., "Fetal Cells in the Blood of Pregnant Women: Detection and Enrichment by Fluorescence-Activiated Cell Sorting," *PNAS, USA* 76:3:1453-1455 (Mar. 1979).

Hoeltke, H. et al., "Multiple Nucleic Acid Labeling and Rainbow Detection," *Analytical Biochemistry* 207:24-31 (1992).

Holden et al., "Amplified Sequences from Chromosome 15, Including Centromeres, Nucleolar Organizer Regions, and Centromeric Heterochromatin, in Homogeneously Staining Regions in the Human Melanoma Cell Line MeWo," *Cancer Genet. & Cytogenet.* 14:131-146 (1985).

Hood et al., *Molecular Biology of Eucaryotic Cells*, W.A. Benjamin, Inc., Menlo Park, CA, pp. 47-51 (1975).

Houlsworth et al., "Comparative Genomic Hybridization: An Overview," *Am. J. Pathology* 145:6:1252-1260 (1994).

Jabs et al., "Characterization of a Cloned DNA Sequence that is Present at Centromeres of All Human Autosomes and the X Chromosome and Shows Polymorphic Variation," *PNAS, USA* 81:4884-4888 (Aug. 1984).

John et al., "RNA-DNA Hybrids at the Cytological Level," *Nature* 223:582-587 (Aug. 1969).

Joos, S. et al., "Mapping and Chromosome Analysis: the Potential of Fluorescence In Situ Hybridization," *Journal of Biotechnology* 35:135-153 (1994).

Kallioniemi et al., "Comparative Genomic Hybridization for Molecular Cytogenetic Analysis of Solid Tumors," *Science* 258:818-821 (1992).

Kallioniemi et al., "Optimizing Comparative Genomic Hybridization for Analysis of DNA Sequence Copy Number Changes in Solid Tumors," *Genes, Chromosomes, and Cancer* 10:231-243 (1994).

Kao et al., "Assignment of the Structural Gene Coding for Albumin to Human Chromosome 4," *Human Genetics* 62:337-341 (1982).

Kievits et al., "Direct Nonradioactive In Situ Hybridization of Somatic Cell Hybrid DNA to Human Lymphocyte Chromosomes," *Cytometry* 11:105-109 (1990).

Krumlauf et al., "Construction and Characterization of Genomic Libraries From Specific Human Chromosomes," *PNAS* 79:2971-2975 (1982).

Kuhlmann, *Immuno Enzyme Techniques in Cytochemistry*, Verlag Chemie, Weinheim, Basel (1984) (Table of Contents only).

Kunkel et al., "Organization and Heterogeneity of Sequences Within a Repeating Unit of Human Y Chromosome Deoxyribonucleic Acid," *Biochem.* 18:3343-3353 (1979).

Landegent et al., "Use of Whole Cosmid Cloned Genomic Sequences for Chromosomal Localization of Non-Radioactive in situ Hybridization," *Hum. Genet.*, 77:366-370 (1987).

Landegent et al., "Chromosomal Localization of a Unique Gene by Non-autoradiographic in situ Hybridization," *Nature* 317:175-177 (Sep. 1985).

Landegent et al., "2-Acetylaminofluorene-Modified Probes for the Indirect Hybridocytochemical detection of Specific Nucleic Acid Sequences," *Exp. Cell Res.*, 153:61-72 (1984).

Landegent et al., "Fine Mapping of the Huntington Disease Linked D4S10 Locus By Non-radioactive in situ Hybridization," *Human Genetics* 73:354-357 (1986).

Landegren et al., "DNA Diagnostics—Molecular Techniques and Automation," *Science* 242:229-237 (Oct. 1988).

Langer-Safer et al., "Immunological Method for Mapping Genes on *Drosphila* Polytene Chromosomes," *PNAS, USA* 79:4381-4385 (1982).

Lawn et al., "The Isolation and Characterization of Linked δ- and β-Globin Genes From a Cloned Library of Human DNA," *Cell* 15:1157-1174 (1978).

Lawrence et al., "Sensitive, High-Resolution Chromatin and Chromosome Mapping In Situ: Presence and Orientation of Two Closely Integrated Copies of EBV in a Lymphoma Line," *Cell* 52:51-61 (Jan. 1988).

LeGrys et al., "Clinical Applications of DNA Probes in the Diagnosis of Genetic Diseases," *CRC Crit. Rev. Clin. Lab. Sci.*, 25:4:255-274 (1987).

Lewin, "Genetic Probes Become Ever Sharper—Rapid Detection of Multiple-Pathogen Infections, Including Major Drug-Resistance Genes, May Be Possible Using A Newly Developed Technique," *Science* 221:4616:1167 (Sep. 1983).

Lichter et al., "Delineation of Individual Human Chromosomes in Metaphase and Interphase Cells By In Situ Suppression Hybridization Using Recombinant DNA Libraries," *Human Genetics* 80:224-234 (1988).

Lichter et al., "Rapid Detection of Human Chromosome 21 Aberrations by in situ Hybridization," *PNAS, USA* 85:9664-9668 (Dec. 1988).

Lichter et al., "High-Resolution Mapping of Human Chromosome 11 by in situ Hybridization with Cosmid Clones," *Science* 247:64-691 (Jan. 5, 1990).

Lichter et al., "Is Non-Isotopic in situ Hybridization Finally Coming of Age?" *Nature* 345:93-94 (May 1990).

Litt et al., "A Highly Polymorphic Locus in Human DNA Revealed by Cosmid-Derived Probes," *PNAS, USA* 82:6206-6210 (Sep. 1985).

Litt et al., "A Highly Polymorphic Locus in Human DNA Revealed by Probes From Cosmid 1-5 Maps to Chromosome 2q35-37," *Am. J. Hum. Gent.* 38:288-296 (1986).

Litt et al., "A Polymorphic on the Long Arm of Chromosome 20 Defined by Two Probes From a Single Cosmid," *Human Genetics* 73:340-345 (1986).

LLNL, "Fluorescent Labeling of Human Chromesomes With Recombinant DNA Probes," *Energy & Tech. Review* 84-85 (Jul. 1985).

LLNL, "Chromosome-Specific Human Gene Libraries," *Energy & Tech. Review* 82-83 (Jul. 1985).

Lucas et al., "Rapid Translocation Analysis Using Fluorescence In Situ Hybridization: Applied to Long Term Biological Dosimetry," (UCRL 102265 Abstract) Radiation Research Meeting, New Orleans, Louisiana (Apr. 7, 1990-Apr. 12, 1990).

Lysov, Y.P. et al., "Determination of the Nucleotide Sequence of DNA Using Hybridization with Oligonucleotides, A New Method,"

*Doklady Biochemistry* 303:436-438, translated from *Doklady Akademii Nauk SSSR* 303:1508-1511 (1988).

Malcolm et al., "Chromosomal Localization of a Single Copy Gene By in situ Hybridization—Human β Globin Genes on the Short Arm of Chromosome 11," *Ann. Hum. Genet.* 45:134-141 (1981).

Maniatis et al., "In vitro Packaging of Bacteriophage λ DNA," *Molecular Cloning: A Laboratory Manual*, Cold Spring Harbor Laboratory, pp. 256-307 (1982).

Maneulidis, "Individual Interphase Chromosome Domains Revealed by in situ Hybridization," *Hum. Genet.* 71:288-293 (1985).

Manuelidis et al., "Chromosomal and Nuclear Distribution of the HindIII 1.9-kb Human DNA Repeat Segment," *Chromosoma (Berl.)* 91:28-38 (1984).

Manuelidis et al., "Different Central Nervous System Cell Types Display Distinct and Nonrandom Arrangements of Satellite DNA Sequences," *PNAS (USA)* 81:3123-3127 (May 1984).

Marmur, "A Procedure for the Isolation of Deoxyribonucleic Acid from Micro-organisms," *J. Mol. Biol.* 3:208-218 (1961).

McCormick, "The Polymerase Chain Reaction and Cancer Diagnosis," *Cancer Cells* 1:2:56-61 (Oct. 1989).

Montgomery et al., "Specific DNA Sequence Amplification in Human Neuroblastona Cells," *PNAS USA* 80:5724-5728 (Sep. 1983).

Nederlof et al., "Detection of Chromosome Aberrations in Interphase Tumor Nuclei by Nonradioactive In Situ Hybridization," *Cancer Genet. Cytogenet.* 42:87-98 (1989).

Nederlof, P.M. et al., "Fluorescence Ratio Measurements of Double-Labeled Probes for Muliple In Situ Hybridization by Digital Imaging Microscopy," *Cytometry* 13:839-845 (1992).

Nederlof, P.M. et al., "Quantification of Inter- and Intra-Nuclear Variation of Fluorescence In Situ Hybridization Signals," *Cytometry* 13:831-838 (1992).

Nelson et al., "Genomic Mismatch Scanning: A New Approach to Genetic Linkage Mapping," *Nature Genetics* 4:11-18 (1993).

Olsen et al., "Isolation of Unique Sequence Human X Chromosomal Deoxyribonucleic Acid," *Biochemistry* 19:2419-2428 (1980).

Park et al., "Amplification, Overexpression and Management of the erb Protoncogene in . . ." *Canc. Res.* 49:6605-6609 (Dec. 1, 1989).

Phillips, J.M. et al., "Multi-color Fluorescence In Situ Hybridization With Early Replicating DNA Libraries," *Proceedings of the American Association for Cancer Research* 35:A3450 Abstract (1994).

Pierce et al., "Analysis of a Dispersed Repetitive DNA Sequence in Isogenic Lines of Drosophila," *Chromosoma* 82:471-492 (1981).

Pinkel et al., "Detection of Structural Chromosome Aberrations in Metaphase Spreads and Interphase Nuclei by in situ Hybridization High Complexity Probes Which Stain Entire Human Chromosomes," *Am. J. Hum. Genet.* (Supplement) 43:3:A118 (Abstract 0471:11.5) (Sep. 1988).

Pinkel et al., "Cytogenetic Analysis Using Quantitative, High-Sensitivity, Fluorescence Hybridization," *PNAS (USA)* 83:2934-2938 (May 1986).

Pinkel et al., "Cytogenetic Analysis By In Situ Hybridization With Fluorescently Labeled Nucleic Acid Probes," *Cold Spring Harbor Symposia on Quantitative Biology*, vol. LI: 151-157 (1986).

Pinkel et al., "Genetic Analysis by Quantitative Microscopy and Flow Cytometry Using Fluorescence In Situ Hybridization With Chromosome-Specific Nucleic Acid Probes," *Am. J. Hum. Genet.* (Supplement) 39:3:A129 (379)(Sep. 1986).

Pinkel et al., "Cytogenetic Analysis During Leukemia Therapy Using Fluorescence in situ Hybridization With Chromosome-Specific Nucleic Acid Probes," *Am. J. Hum. Genet.* (Supplement) 41:3:A34 (096;12.12) (Sep. 1987).

Pinkel et al., "Simplified Cytogenetics Using Biotin Labeled Nucleic Acid Probes and Quantative Fluorescence Microscopy," *Am. J. Hum. Genet.* (Supplement) 37:4:A112 (328; 17.2) (Jul. 1985).

Pinkel et al., "Fluorescene In Situ Hybridization with Human Chromosome-Specific Libraries: Detection of Trisomy 21 and Translocations of Chromosome 4," *PNAS (USA)*, 85:9138-9142 (Dec. 1988).

Pinkel et al., "Cytogenetics Using Fluorescent Nucleic Acid Probes and Quantitative Microscopic Measurement," (UCRL 93269 Abstract) Analytical Cytology X Conference, Hilton Head Resort, Hilton Head Island, S.C. (Nov. 17, 1985-Nov. 22, 1985).

Pinkel et al., "Rapid Quantitative Cytogenic Analysis Using Fluorescently Labeled Nucleic Acid Probes," (UCRL 93553 Abstract), U.S.—Japan Joint Environmental Panel Conf., Research Triangle Park, N.C. (Oct. 21, 1985-Oct. 23, 1985).

Pinkel et al., "Detection of Structural and Numerical Abnormalities in Metaphase Spreads and Interphase Nuclei Using In Situ Hybridization," *Cancer Genet. And Cytogenet.* (UCRL 101043 Abstract) 41:236 (Oct. 1989).

Pinkel et al., "Simplified Cytogenetics Using Biotin Labeled Nucleic Acid Probes and Quantitative Fluorescence Microscopy," (UCRL 93243 Abstract), *American Journal of Human Genetics* (Supplement), 37:A112 (Jul. 1985).

Pinkel et al., "Detection of Translocations and Aneuploidy in Metaphase Spreads and Interphase Nuclei by In Situ Hybridization with Probes Which Stain Entire Human Chromosomes," (UCRL 101042 Abstract) 21st Oak Ridge Conference on Advanced Concepts in the Clinical Laboratory, (Apr. 13, 1989-Apr. 14, 1989).

Rabin et al., "Mapping Minimally Reiterated Genes on Diploid Chromosomes by in situ Hybridization," Thesis, Dept. of Biochemistry, Univ. Ill. (1982).

Rabin et al., "Two Homeo Box Loci Mapped in Evolutionarily Related Mouse and Human Chromosomes," *Nature* 314:175-178 (1985).

Rappold et al., "Sex Chromosome Positions in Human Interphase Nuclei as Studied By In Situ Hybridization With Chromosome Specific DNA Probes," *Human Genetics* 67: 317-322 (1984).

Renz, M., "Polynucleotide-Histone H1 Complexes as Probes for Blot Hybridization," *EMBO Journal* 2:6:817-822 (1983).

Renz, M. and Kurz, C., "A Colorimetric Method for DNA Hybridization," *Nucleic Acids Research* 12:8:3435-44 (1984).

Richardson et al. "Biotin and Fluorescent Labeling of RNA Using T4 RNA Ligase," *Nucleic Acids Research* 11:18:6167-6184 (1983).

Ried et al., "Simultaneous Visualization of Seven Different DNA Probes by in situ Hybridization Using Combinatorial Fluorescence and Digital Imaging Microscopy," *Proc. Natl. Acad. Sci. USA* 89:1388-1392 (Feb. 1992).

Roelofs et al., "Gene Amplification in Human Cells May Involve Interchromosomal Transposition and Persistance of the Oringinal DNA Region," *The New Biologist* 4:1:75-86 (Jan. 1992).

Ruddle, "A New Era in Mammalian Gene Mapping: Somatic Cell Genetics and Recombinant DNA Methodologies," *Nature* 294:115-120 (1981).

Sain-Ruf et al., "Proto-Oncogene Amplification and Homogeneously Staining Regions in Human Breast Carcinomas," *Genes, Chromosomes & Cancer* 2:18-26 (1990).

Scalenghe et al., "Microdissection and Cloning of DNA from a Specific Region of Drosophila melanogaster Polytene Chromosomes," *Chromosoma (Berl.)* 82:205-216 (1981).

Schardin et al., "Specific Staining of Human Chromsomes in Chinese Hamster X Man Hybrid Cell Lines Demonstrates Interphase Chromosome Territories," *Hum. Genet.* 71: 281-287 (1985).

Schmeckpeper et al., "Partial Purification and Characterization of DNA from the Human X Chromosome," *PNAS (USA)* 76:12:6525-6528 (Dec. 1979).

Sealey et al., "Removal of Repeated Sequences from Hybridisation Probes," *Nucleic Acid Research* 13:6:1905-1922 (1985).

Selypes et al., "A Noninvasive Method for Determination of the Sex and Karyotype of the Fetus From the Maternal Blood," *Hum. Genet.* 79:357-359 (1988).

Siracusa et al., "Use of Repetitive DNA Sequences to Distinguish *Mus musculus* and *Mus caroli* Cells by in situ Hybridization," *J. Embryol. Exp. Morph.* 73:163-178 (1983).

Skolnick, M.H. and Wallace, R.B., "Simultaneous Analysis of Multiple Polymorphic Loci Using Amplified Sequence Polymorphisms (ASPs)" *Genomics* 2:273-279 (1988).

Smith et al., "Distinctive Chromosomal Structures are Formed Very Early in the Amplification of CAD Genes in Syrian Hamster Cells," *Cell* 63:1219-1227 (Dec. 21, 1990).

Smith, L.M. et al., "The Synthesis of Oligonucleotides Containing an Aliphatic Amino Group at the 5' Terminus: Synthesis of Fluorescent DNA Primers for Use in DNA Sequence Analysis," *Nucleic Acids Research* 13:2399-2412 (1985).

Sondermeijer et al., "The Activity of Two Heat Shock Loci of *Drosophila hydrei* in Tissue Culture Cells and Salivary Gland Cells as Analyzed by in situ Hybridization of Complementary DNA," *Chromosoma* 72:281-291 (1979).

Southern, E.M. et al., "Analyzing and Comparing Nucleic Acid Sequences by Hybridization to Arrays of Oligonucleotides: Evaluation Using Experimental Models," *Genomics* 13:1008-1017 (1992).

Sparks et al., "Regional Assignment of Genes for Human Esterase D and Retinoblastoma to Chromosome Band 13q14," *Science* 208:1042-1044 (May 30, 1988).

Steinemann et al., "Multiple Sex Chromosomes in *Drosophila miranda*: A System to Study the Degeneration of a Chromosome," *Chromosoma* 86:59-76 (1982).

Stewart et al., "Cloned DNA Probes Regionally Mapped to Human Chromosome 21 and Their Use in Determining the Origin of Nondisjunction," *Nucleic Acids Research* 13:11:4125-4132 (1985).

Straume et al., "Chromosome Translocation of Low Radiation Doses Quantified Using Fluorescent DNA Probes," (UCRL 93837 Abstract), Radiation Research Society Meeting, Las Vegas, Nevada (Apr. 12, 1986-Apr. 17, 1986).

Szabo et al., "What's New With Hybridization in situ?" *TIBS* 7:11:425-427 (Dec. 1982).

Szabo et al., "Quantitative in situ Hybridization of Ribosomal RNA Species to Polytene Chromosomes of *Drosophila melanogaster*," *J. Mol. Biol.* 115:539-563 (1977).

Tchen et al., "Chemically Modified Nucleic Acids as Immunodetectable Probes in Hybridization Experiments," *PNAS* 81:3466-3470 (1984).

Thompson et al., *Thompson & Thompson: Genetics in Medicine*, 5th ed., W.B. Saunders Co., Philadelphia, PA, 38-39 (1991).

Tkachuk, D.C. et al., "Clinical Applications of Fluorescence in situ Hybridization," *GATA* 8:2:67-74 (1991).

Trask et al., "The Proximity of DNA Sequences in Interphase Cell Nuclei Is Correlated to Genomic Distance and Permits Ordering of Cosmids Spanning 250 Kilobase Pairs," *Genomics* 5:710-717 (1989).

Trask et al., "Detection of DNA Sequences in Nuclei in Suspension by In Situ Hybridization and Dual Beam Flow Cytometry," (UCRL 93372 Abstract) Analytical Cytology X Conference, Hilton Head Resort, Hilton Head Island, S.C. (Nov. 17, 1985-Nov. 22, 1985).

Trask et al., "Early Dihydrofolate Reductase Gene Amplification Events in CHO Cells Usually Occur on the Same Chromosome Arm as the Original Locus," *Genes & Development* 3:1913-1925 (1989).

Trent et al., "Report of the Committee on Structural Chromosome Changes in Neoplasia," *Cytogent. Cell Genet.* 51:533-562 (1989).

Van Dilla et al., "Construction and Availability of Human Chromosome-Specific DNA Libraries From Flow Sorted Chromosomes: Status Report," *Am. J. of Hum. Genetics* 37:A179 (R Supplement) (Jul. 1985).

Wallace et al., "The Use of Synthetic Oligonucleotides as Hybridization Probes—II Hybridization of Oligonucleotides of Mixed Sequence to Rabbit β Globin DNA," *Nucleic Acids Research* 9:4:879-894 (1981).

Weiss et al., "Organization and Evolution of the Class I Gene Family in the Major Histocompatibility Complex of the C57BL/10 Mouse," *Nature* 310:23:650-655 (Aug. 1984).

Willard et al., "Isolation and Characterization of a Major Tandem Repeat Family from the Human X Chromosome," *Nucleic Acids Research* 11:7:2017-2033 (1983).

Windle et al., "A Central Role for Chromosome Breakage in Gene Amplification, Deletion Formation, and Amplicon Integration," *Genes & Development* 5:160-174 (1991).

Yunis et al., "Localization of Sequences Specifying Messenger RNA to Light-Staining G-Bands of Human Chromosomes," *Chromosoma (Berl.)* 61:335-344 (1977).

Grant Application (1997) "Genome Wide Analysis of DNA Copy Number By Array CGH" Dept of Health and Human Services Public Health Services.

* cited by examiner

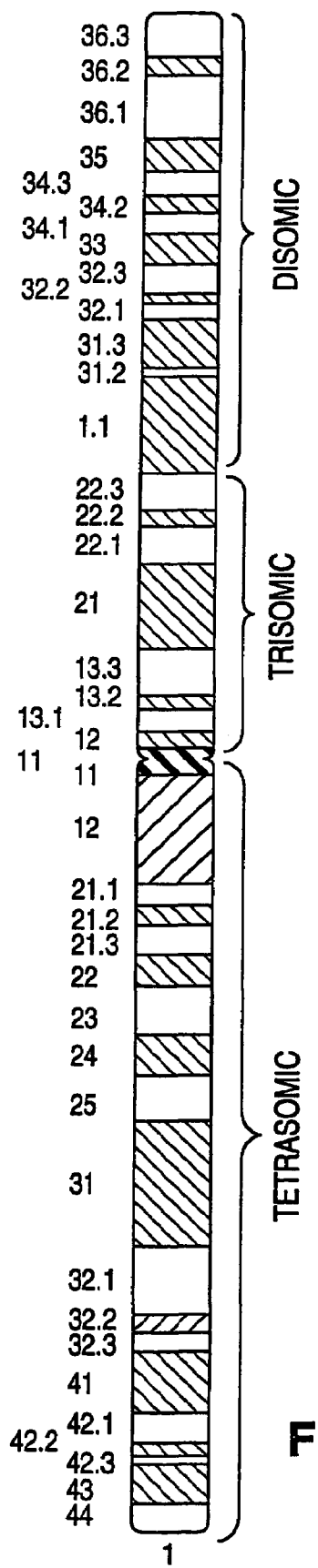
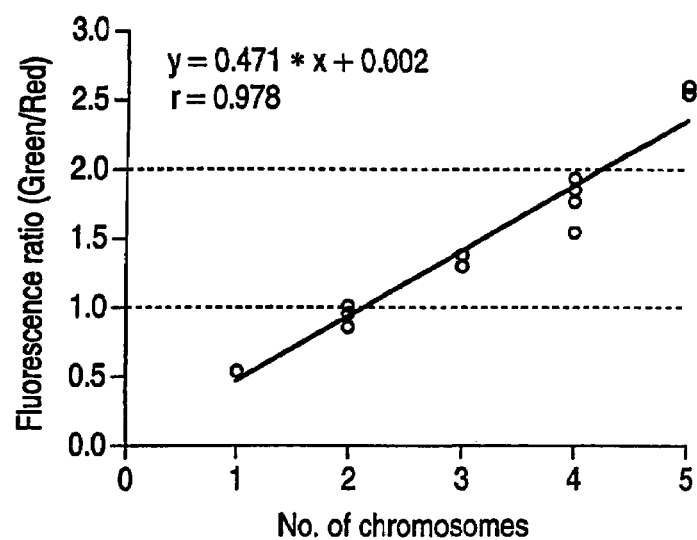
FIG. 10B
FIG. 9

COMPARATIVE GENOMIC HYBRIDIZATION

RELATED APPLICATIONS

This application is a continuation of U.S. Ser. No. 11/017,493, filed on Dec. 17, 2004, now U.S. Pat. No. 7,238,484 which is a continuation of U.S. Ser. No. 09/644,140, filed on Aug. 22, 2000, now abandoned which is a continuation of U.S. Ser. No. 08/903,095, filed on Jul. 30, 1997, now U.S. Pat. No. 6,159,685, which is a continuation of U.S. Ser. No. 08/468,629, filed on Jun. 6, 1995, now U.S. Pat. No. 5,721,098, which is a continuation of U.S. Ser. No. 08/166,147, filed on Dec. 14, 1993, now abandoned, which is a continuation of U.S. Ser. No. 07/969,948, filed on Oct. 30, 1992, now abandoned, which is a continuation-in-part of U.S. Ser. No. 07/846,659, filed Mar. 4, 1992, now abandoned. Each of the applications cited above is incorporated by reference in its entirety.

This invention was made with Government support under Grant Nos. CA-45919 and CA-44768, awarded by the National Institute of Health. The Government has certain rights in this invention.

FIELD OF THE INVENTION

This invention relates generally to the field of cytogenetics, and more particularly to the field of molecular cytogenetics. It concerns methods of determining the relative copy numbers of different nucleic acid sequences in a subject cell or cell population and/or comparing the nucleic acid sequence copy numbers of substantially identical sequences in several cells or cell populations as a function of the location of those sequences in a reference genome. For instance, the methods of this invention provide the means to determine the relative number of copies of nucleic acid sequences in one or more subject genomes (for example, the DNA of one tumor cell or a number of cells from a subregion of a solid tumor) or portions thereof as a function of the location of those sequences in a reference genome (for example, a normal human metaphase spread). Further, the invention provides methods of determining the absolute copy number of nucleic acid sequences in a subject cell or cell population.

Although the examples herein concern human cells and the language is primarily directed to human concerns, the concept of this invention is applicable to genomes from any plant or animal. The genomes compared need only be related closely enough to have sufficient substantially identical sequences for a meaningful analysis. For example, a human genome and that of another primate could be compared according to the methods of this invention.

BACKGROUND OF THE INVENTION

Chromosome abnormalities are associated with genetic disorders, degenerative diseases, and exposure to agents known to cause degenerative diseases, particularly cancer, German, "Studying Human Chromosomes Today," *American Scientist*, 58: 182-201 (1970); Yunis; "The Chromosomal Basis of Human Neoplasia," *Science*, 221: 227-236 (1983); and German, "Clinical Implication of Chromosome Breakage," in *Genetic Damage in Man Caused by Environmental Agents*, Berg, Ed., pgs. 65-86 (Academic Press, New York, 1979). Chromosomal abnormalities can be of several types, including: extra or missing individual chromosomes, extra or missing portions of a chromosome (segmental duplications or deletions), breaks, rings and chromosomal rearrangements, among others. Chromosomal or genetic rearrangements include translocations (transfer of a piece from one chromosome onto another chromosome), dicentrics (chromosomes with two centromeres), inversions (reversal in polarity of a chromosomal segment), insertions, amplifications, and deletions.

Detectable chromosomal abnormalities occur with a frequency of one in every 250 human births. Abnormalities that involve deletions or additions of chromosomal material alter the gene balance of an organism and generally lead to fetal death or to serious mental and physical defects. Down syndrome can be caused by having three copies of chromosome 21 instead of the normal 2. This syndrome is an example of a condition caused by abnormal chromosome number, or aneuploidy. Down syndrome can also be caused by a segmental duplication of a subregion on chromosome 21 (such as, 21q22), which can be present on chromosome 21 or on another chromosome. Edward syndrome (18+), Patau syndrome (13+), Turner syndrome (XO) and Kleinfelter syndrome (XXY) are among the most common numerical aberrations. [Epstein, *The Consequences of Chromosome Imbalance: Principles, Mechanisms and Models* (Cambridge Univ. Press 1986); Jacobs, *Am. J. Epidemiol*, 105: 180 (1977); and Lubs et al., *Science*, 169: 495 (1970).]

Retinoblastoma (del 13q14), Prader-Willis syndrome (del 15q11-q13), Wilm's tumor (del 11p13) and Cri-du-chat syndrome (del 5p) are examples of important disease linked structural aberrations. [Nora and Fraser, *Medical Genetics: Principles and Practice*, (Lea and Febiger (1989).]

One of the critical endeavors in human medical research is the discovery of genetic abnormalities that are central to adverse health consequences. In many cases, clues to the location of specific genes and/or critical diagnostic markers come from identification of portions of the genome that are present at abnormal copy numbers. For example, in prenatal diagnosis, as indicated above, extra or missing copies of whole chromosomes are the most frequently occurring genetic lesion. In cancer, deletion or multiplication of copies of whole chromosomes or chromosomal segments, and higher level amplifications of specific regions of the genome, are common occurrences.

Much of such cytogenetic information has come over the last several decades from studies of chromosomes with light microscopy. For the past thirty years cytogeneticists have studied chromosomes in malignant cells to determine sites of recurrent abnormality to glean hints to the location of critical genes. Even though cytogenetic resolution is limited to several megabases by the complex packing of DNA into the chromosomes, this effort has yielded crucial information. Among the strengths of such traditional cytogenetics is the ability to give an overview of an entire genome at one time, permitting recognition of structural abnormalities such as inversions and translocations, as well as deletions, multiplications, and amplifications of whole chromosomes or portions thereof. With the coming of cloning and detailed molecular analysis, recurrent translocation sites have been recognized as involved in the formation of chimeric genes such as the BCR-ABL fusion in chronic myelogeneous leukemia (CML); deletions have been recognized as frequently indicating the location of tumor suppressor genes; and amplifications have been recognized as indicating overexpressed genes.

Conventional procedures for genetic screening and biological dosimetry involve the analysis of karyotypes. A karyotype is the particular chromosome complement of an individual or of a related group of individuals, as defined both by the number and morphology of the chromosomes usually in mitotic metaphase. It include such things as total chromosome number, copy number of individual chromosome types (e.g., the number of copies of chromosome X), and chromosomal morphology, e.g., as measured by length, centromeric index, connectedness, or the like. Karyotypes are conventionally determined by chemically staining an organism's metaphase, prophase or otherwise condensed (for example, by premature chromosome condensation) chromosomes. Condensed chromosomes are used because, until recently, it has not been possible to visualize interphase chromosomes due to their dispersed condition and the lack of visible boundaries between them in the cell nucleus.

A number of cytological techniques based upon chemical stains have been developed which produce longitudinal patterns on condensed chromosomes, generally referred to as bands. The banding pattern of each chromosome within an organism usually permits unambiguous identification of each chromosome type [Latt, "Optical Studies of Metaphase Chromosome Organization," *Annual Review of Biophysics and Bioengineering,* 5: 1-37 (1976)].

Unfortunately, such conventional banding analysis requires cell culturing and preparation of high quality metaphase spreads, which is time consuming and labor intensive, and frequently difficult or impossible. For example, cells from many tumor types are difficult to culture, and it is not clear that the cultured cells are representative of the original tumor cell population. Fetal cells capable of being cultured, need to be cultured for several weeks to obtain enough metaphase cells for analysis.

Over the past decade, methods of in situ hybridization have been developed that permit analysis of intact cell nuclei—interphase cytogenetics. Probes for chromosome centromeres, whole chromosomes, and chromosomal segments down to the size of genes, have been developed. With the use of such probes, the presence or absence of specific abnormalities can be very efficiently determined; however, it is tedious to test for numerous possible abnormalities or to survey to discover new regions of the genome that are altered in a disease.

The present invention, Comparative Genomic Hybridization (CGH) [formerly called Copy Ratio Reverse Cytogenetics (CRRC) among other names] provides powerful methods to overcome many of the limitations of existing cytogenetic techniques. When CGH is applied, for example, in the fields of tumor cytogenetics and prenatal diagnosis, it provides methods to determine whether there are abnormal copy numbers of nucleic acid sequences anywhere in the genome of a subject tumor cell or fetal cell or the genomes from representative cells from a tumor cell population or from a number of fetal cells, without having to prepare condensed chromosome spreads from those cells. Thus, cytogenetic abnormalities involving abnormal copy numbers of nucleic acid sequences, specifically amplifications and/or deletions, can be found by the methods of this invention in the format of an immediate overview of an entire genome or portions thereof. More specifically, CGH provides methods to compare and map the frequency of nucleic acid sequences from one or more subject genomes or portions thereof in relation to a reference genome. It permits the determination of the relative number of copies of nucleic acid sequences in one or more subject genomes (for example, those of tumor cells) as a function of the location of those sequences in a reference genome (for example, that of a normal human cell).

Gene amplification is one of several mechanisms whereby cells can change phenotypic expression when increased amounts of specific proteins are required, for example, during development [Spradling and Mahowald, *PNAS (USA),* 77: 1096-1100 (1980); Glover et al., *PNAS (USA),* 79: 2947-2951 (1982)], or during an environmental challenge when increased amounts of specific proteins can impart resistance to cytotoxic agents [Melera et al., *J. Biol. Chem,* 255: 7024-7028 (1980); Beach and Palmiter, *PNAS (USA,* 78: 2110-2114 (1981)].

A major limitation of Southern analysis and related conventional techniques for analysis of gene amplification is that only specific sites are studied leaving the vast majority of the genome unexamined. Conventional cytogenetic studies, on the other hand, provide a broad survey of the genome but provide little information about genes that may be involved in amplification events. However, the procedures of this invention overcome those limitations. This invention can be used to show the normal chromosomal locations of all regions of a genome that are amplified or deleted wherein the size of the regions that can be detected is limited only by the resolution of the microscopy used and the organization of DNA in condensed chromosomes. Thus, this invention provides among other uses the ability to study gene amplifications and deletions and their roles in tumor development, progression and response to therapy more thoroughly than was possible previously. The methods of CGH are sufficiently rapid and simple that large numbers of subject nucleic acids, for example from many tumors, can be analysed in studies for gene amplification and deletion.

The karyotypic heterogeneity in solid tumors can be extreme. Identification of commonly occurring chromosomal changes by analysis of metaphase spreads is often difficult or impossible using conventional banding analysis because of the complexity of the rearrangements and because of the poor quality of the metaphase preparations. CGH overcomes that limitation in that the tumor nucleic acid can be studied without the requirement of preparing metaphase spreads. Since CGH can probably be performed on single cells by amplifying the nucleic acid therefrom, CGH can be used to investigate the heterogeneity of tumors by studying representative cells from different cell populations of the tumor. Alternatively, CGH of nucleic acid from a tumor extracted in a bulk extraction process from many cells of the tumor can reveal consistencies within the apparent heterogeneity. For example, the same amplified sequences may appear as homogeneously staining regions (HSRs) and/or double minute chromosomes (DMs) in one tumor cell but as an extension of a chromosome arm in another tumor cell. Thus, order from the apparent randomness may be realized by CGH hybridization.

Montgomery et al., *PNAS (USA),* 80: 5724-5728 (September 1983), concerns the hybridization of labeled Cot fractionated DNAs from tumor cell lines (a Cot fraction from which the high copy repeats, low copy repeats and single copy sequences were substantially removed) to metaphase spreads from said tumor cell lines. Basically, Montgomery et al. mapped the positions of nucleic acid sequences from tumor cell lines that are very highly amplified back to tumor cell line genomes.

Total genomic DNA from one species has been used in in situ hybridization to discriminate in hybrid cells between chromosomes of that species and of a different species on the basis of the signal from the high copy repetitive sequences. [Pinkel et al., *PNAS (USA),* 83: 2934 (1986); Manuelidis, *Hum. Genet.,* 71: 288 (1985); and Durnam et al., *Somatic Cell Molec. Genet.,* 11: 571 (1985).]

Landegent et al., *Hum. Genet.,* 77: 366-370 (1987) eliminated highly repetitive sequences, like Alu and Kpn fragments, from whole cosmid cloned genomic sequences by blocking the highly repetitive sequences with Cot-1 DNA. The resulting probe was used for in situ hybridization.

European Patent Application Publication No. 430,402 (published Jun. 5, 1991) describes methods and compositions for chromosome-specific painting, that is, methods and compositions for staining chromosomes based upon nucleic acid sequence employing high complexity nucleic acid probes. In general in the chromosome-specific painting methods, repetitive sequences not specific to the targeted nucleic acid sequences are removed from the hybridization mixture and/or their hybridization capacity disabled, often by blocking with unlabeled genomic DNA or with DNA enriched for high copy repetitive sequences as is Cot-1 [commercially available from Bethesda Research Laboratory, Gaithersburg, Md. (USA)]. Pinkel et al., *PNAS (USA),* 85: 9138-9142 (1988) also describes aspects of chromosome-specific painting as well as International Publication No. WO 90/05789 (published May 31, 1990 entitled "in situ Suppression Hybridization and Uses Therefor").

Chromosome-specific repeat sequence probes and chromosome-specific painting probes can be hybridized in situ to interphase nuclei as well as metaphase spreads and provide information about the genetic state of the individual targeted genomes. A limitation of such hybridizations is that cytogenetic information is only provided from the regions to which the probes bind. Such hybridizations are very useful for determining if a particular abnormality is present, for example, the deletion of a specific gene or a duplication among other abnormalities, but it is laborious to search for currently unknown abnormalities on a region by region basis.

Other methods of searching for unknown genetic abnormalities similarly require a lot of work. For example, looking for loss of heterozygosity in tumor cells, requires the hybridization of many probes to Southern blots of tumor and normal cell DNA. The instant invention, Comparative Genomic Hybridization (CGH), provides methods to overcome many of the limitations of the existing cytogenetic techniques.

Saint-Ruf et al., *Genes, Chromosomes & Cancer,* 2: 18-26 (1990) state at page 24 that > Human breast carcinomas are characterized by two sets of molecular anomalies. Firstly, some proto-oncogenes, such as MYC, INT2, HST, and ERBB2, are frequently found either amplified or overexpressed.... Secondly, loss of heterozygosity has been reported, especially for 1p, 11, 13 and 17 . . .
>
> Human breast carcinomas are also characterized cytogenetically by various anomalies that may be the chromosomal counterpart of the molecular anomalies: regions of amplification (HSRs) are found in more than one-third of the tumors . . . , and various deletions, affecting, e.g., 1p, 11p, 11q, 13, and 17p, are found recurrently....

[Citations omitted.] Saint-Ruf et al. concluded from the reported experiments that although amplification of genetic material is a frequent and probably important event in breast carcinogenesis, that the relevant genes involved in such amplifications remain unknown but do not seem to correspond to the proto-oncogenes commonly considered important in breast cancer.

Since HSRs in tumors are most often not at the site of the amplified gene(s) in normal cells, standard cytogenetics does not yield any information that could assist with identification of the gene(s). CGH on the other hand permits mapping them in the normal genome, a major step towards their identification.

Dutrillaux et al., *Cancer Genet. Cytogenet.,* 49: 203-217 (1990) report (at page 203) that "[a]lthough human breast carcinomas are among the most frequent malignant tumors, cytogenetic data remain scarce, probably because of their great variability and of the frequent difficulty of their analysis." In their study of "30 cases with relatively simple karyotypes to determine which anomalies occur the most frequently and, in particular, early during tumor progression" (p. 203), they concluded that "trisomy 1q and monosomy 16q are early chromosomal changes in breast cancer, whereas other deletions and gain of 8q are clearly secondary events." [*Abstract*, p. 203.] Dutrillaux et al. further state (at page 216) that deletions within tumor suppressor genes "characterize tumor progression of breast cancer."

It is believed that many solid tumors, such as breast cancer, progress from initiation to metastasis through the accumulation of several genetic aberrations. [Smith et al., *Breast Cancer Res. Treat.,* 18 Suppl. 1: S 5-14 (1991); van de Vijver and Nusse, *Biochim. Biophys. Acta,* 1072: 33-50 (1991); Sato et al., *Cancer Res.,* 50: 7184-7189 (1990).] Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

Dominantly acting genes associated with human solid tumors typically exert their effect by overexpression or altered expression. Gene amplification is a common mechanism leading to upregulation of gene expression. [Stark et al., *Cell,* 75: 901-908 (1989).] Evidence from cytogenetic studies indicates that significant amplification occurs in over 50% of human breast cancers. [Saint-Ruf et al., supra.] A variety of oncogenes have been found to be amplified in human malignancies. Examples of the amplification of cellular oncogenes in human tumors is shown in Table 1 below.

TABLE 1

| Amplified Gene | Tumor | Degree of Amplification | DM or HSR Present |
|---|---|---|---|
| c-myc | Promyelocytic leukemia cell line, HL60 | 20x | + |
|  | Small-cell lung carcinoma cell lines | 5-30x | ? |
| N-myc | Primary neuroblastomas (stages III and IV) and neuroblastoma cell lines | 5-1000x | + |
|  | Retinoblastoma cell line and primary tumors | 10-200x | + |
|  | Small-cell lung carcinoma cell lines and tumors | 50x | + |
| L-myc | Small-cell lung carcinoma cell lines and tumors | 10-20x | ? |
| c-myb | Acute myeloid leukemia | 5-10x | ? |
|  | Colon carcinoma cell lines | 10x | ? |
| c-erbB | Epidermoid carcinoma cell | 30x | ? |
|  | Primary gliomas |  | ? |
| c-K-ras-2 | Primary carcinomas of lung, colon, bladder, and rectum | 4-20x | ? |

TABLE 1-continued

| Amplified Gene | Tumor | Degree of Amplification | DM or HSR Present |
|---|---|---|---|
| N-ras | Mammary carcinoma cell line | 5-10x | ? |

SOURCE:
modified from Varmus, Ann. Rev. Genetics, 18: 553-612 (1984) [cited in Watson et al., Molecular Biology of the Gene (4th ed.; Benjamin/Cummings Publishing Co. 1987)]

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene [Friend et al., *Nature*, 323: 643 (1986); Lee et al., *Science*, 235: 1394 (1987); Fung et al., *Science*, 236: 1657 (1987)]. The Rb-1 gene product, a 105 kDa nuclear phosphoprotein, apparently plays an important role in cell cycle regulation [Lee et al., supra (1987); Howe et al., *PNAS* (USA), 87: 5883 (1990)]. Altered or lost expression of the Rb protein is caused by inactivation of both gene alleles either through a point mutation or a chromosomal deletion. Rb-1 gene alterations have been found to be present not only in retinoblastomas [Friend et al., supra (1986); Lee et al., supra (1987); Fung et al., supra (1987)] but also in other malignancies such as osteosarcomas [Friend et al., supra (1986)], small cell lung cancer [Hensel et al., *Cancer Res.*, 50: 3067 (1990); Rygaard et al., *Cancer Res.*, 50: 5312 (1990)] and breast cancer [Lee et al., *Science*, 241: 218 (1988); T'Ang et al., *Science*, 242: 263 (1988); Varley et al., *Oncogene*, 4: 725 (1989)]. Restriction fragment length polymorphism (RFLP) studies have indicated that such tumor types have frequently lost heterozygosity at 13q suggesting that one of the Rb-1 gene alleles has been lost due to a gross chromosomal deletion [Bowcock et al., *Am. J. Hum. Genet.*, 46: 12 (1990)].

The deletion of the short arm of chromosome 3 has been associated with several cancers, for example, small cell lung cancer, renal and ovarian cancers; it has been postulated that one or more putative tumor suppressor genes is or are located in the p region of chromosome 3 (ch. 3p) [Minna et al., *Symposia on Quantitative Biology*, Vol. L1: 843-853 (SCH Lab 1986); Cohen et al., *N. Eng. J. Med.*, 301: 592-595 (1979); Bergerham et al., *Cancer Res.*, 49: 1390-1396 (1989); Whang-Peng et al., *Can. Genet. Cytogenet.*, 11: 91-106 (1984; and Trent et al., *Can. Genet. Cytogenet.*, 14: 153-161 (1985)].

The above-indicated collection of amplified and deleted genes is far from complete. As the Saint-Ruf et al. study (supra) of oncogene amplification in cells showing cytogenetic evidence of amplification, such as double minutes (DMs) or homogeneously staining regions (HSRs), indicated, the amplified genes were not known oncogenes in most cases. As Dutrillaux et al., supra indicated, "cytogenetic data remains scarce" for "the most frequent malignant tumors"—breast carcinomas.

Discovery of genetic changes involved in the development of solid tumors has proven difficult. Karyotyping is impeded by the low yield of high quality metaphases and the complex nature of chromosomal changes [Teyssier, J. R., *Cancer Genet. Cytogenet.*, 37: 103 (1989)]. Although molecular genetic studies of isolated tumor DNA have been more successful and permitted detection of common regions of allelic loss, mutation or amplification [Fearon et al., *Cell*, 61: 759 (1990); Sato et al., *Cancer Res.*, 50: 7184 (1990); Alitalo et al., *Adv. Cancer Res.*, 47: 235 (1986); and Schwab and Amler, *Genes Chrom. Cancer.*, 1: 181 (1990)], such molecular methods are highly focused, targeting one specific gene or chromosome region at a time, and leaving the majority of the genome unexamined.

Thus, a research tool leading to the identification of amplified and deleted genes and providing more cytogenetic data regarding tumors, especially tumor progression and invasiveness is needed in tumor cytogenetics. CGH provides such a molecular cytogenetic research tool.

CGH facilitates the genetic analysis of tumors in that it provides a copy number karyotype of the entire genome in a single step. Regions of tumor DNA gain and loss are mapped directly onto normal chromosomes. Comparisons of primary tumors with their metastases by CGH should be informative concerning cancer progression.

The ability to survey the whole genome in a single hybridization is a distinct advantage over allelic loss studies by restriction fragment length polymorphism (RFLP) that target only one locus at a time. RFLP is also restricted by the availability and informativeness of polymorphic probes.

The copy number karyotype determined by CGH may become as important for diagnostic and/or prognostic assessment of solid tumors as conventional karyotyping now is for hematologic malignancies. [Yunis, J. J., *Science*, 221: 227 (1983); Solomon et al., *Science*, 254: 1153 (1991).]

SUMMARY OF THE INVENTION

Comparative Genomic Hybridization (CGH) employs the kinetics of in situ hybridization to compare the copy numbers of different DNA or RNA sequences from a sample, or the copy numbers of different DNA or RNA sequences in one sample to the copy numbers of the substantially identical sequences in another sample. In many useful applications of CGH, the DNA or RNA is isolated from a subject cell or cell population. The comparisons can be qualitative or quantitative. Procedures are described that permit determination of the absolute copy numbers of DNA sequences throughout the genome of a cell or cell population if the absolute copy number is known or determined for one or several sequences. The different sequences are discriminated from each other by the different locations of their binding sites when hybridized to a reference genome, usually metaphase chromosomes but in certain cases interphase nuclei. The copy number information originates from comparisons of the intensities of the hybridization signals among the different locations on the reference genome.

Two representative basic approaches are employed in CGH as illustrated herein for the analysis of subject DNAS. In an example of the first approach, genomic DNA from a subject cell or cell population of cells is isolated, labeled and hybridized to reference chromosomes, usually in metaphase. In an example of the second approach, genomic DNAs from two or more subject cells or cell populations are isolated, differentially labeled, and hybridized to reference chromosomes, usually in metaphase.

The CGH methods of this invention can be qualitative and/or quantitative. A particular utility of CGH is for analysing DNA sequences from subject cell(s) or cell population(s), for example from clinical specimens including tumor and fetal tissues.

An important utility of CGH is to find regions in normal genomes which when altered in sequence copy number contribute to disease, as for example, cancer or birth defects. For example, regions at elevated copy number may contain oncogenes, and regions present at decreased copy number may contain tumor suppressor genes.

A representative CGH method is for comparing copy numbers of different DNA sequences in a subject cell or cell population comprising the steps of:

a) extracting the DNA from the subject cell or from a number of cells of the subject cell population;

b) amplifying said extracted subject DNA, if necessary;

c) labeling the subject DNA;

d) hybridizing said labeled subject DNA in situ to reference metaphase chromosomes after substantially removing from the labeled DNA those repetitive sequences that could bind to multiple loci in the reference metaphase chromosomes, and/or after blocking the binding sites for those repetitive sequences in the reference metaphase chromosomes by prehybridization with appropriate blocking nucleic acids, and/or blocking those repetitive sequences in the labeled DNA by prehybridization with appropriate blocking nucleic acid sequences, and/or including such blocking nucleic acid sequences for said repetitive sequences during said hybridization, wherein the DNA sequences in the labeled subject DNA that bind to single copy sequences in the reference metaphase chromosomes are substantially retained, and those single copy DNA sequences as well as their binding sites in the reference metaphase chromosomes remain substantially unblocked both before and during the hybridization;

e) rendering the bound, labeled DNA sequences visualizable, if necessary;

f) observing and/or measuring the intensity of the signal from the labeled subject DNA sequences as a function of position on the reference metaphase chromosomes; and g) comparing the copy numbers of different DNA sequences of the subject DNA by comparing the signal intensities at different positions on the reference metaphase chromosomes, wherein the greater the signal intensity at a given position, the greater the copy number of the sequences in the subject DNA that bind at that position. An analogous method can be performed wherein the subject nucleic acid is RNA.

Further, disclosed are methods whrein two or more subject nucleic acids are analysed by CGH. Exemplary methods are those wherein the subject nucleic acids are DNA sequences from a subject cell or cell population. Analogous methods may be performed wherein the subject nucleic acids are RNA. Such an exemplary method is that for comparing copy numbers of different DNA sequences in one subject cell or cell population relative to copy numbers of substantially identical sequences in another cell or cell population, said method comprising the steps of:

a) extracting the DNA from both of the subject cells or cell populations;

b) amplifying said extracted subject DNAs, if necessary;

c) differentially labeling the subject DNAs;

d) hybridizing said differentially labeled subject DNAs in situ to reference metaphase chromosomes after substantially removing from the labeled DNAs those repetitive sequences that could bind to multiple loci in the reference metaphase chromosomes, and/or after blocking the binding sites for those repetitive sequences in the reference metaphase chromosomes by prehybridization with appropriate blocking nucleic acids, and/or blocking those repetitive sequences in the labeled DNA by prehybridization with appropriate blocking nucleic acid sequences, and/or including such blocking nucleic acid sequences for said repetitive sequences during said hybridization;

e) rendering the bound, differentially labeled DNA sequences visualizable, if necessary;

f) observing and/or measuring the intensities of the signals from each subject DNA, and the relative intensities, as a function of position along the reference metaphase chromosomes; and g) comparing the relative intensities among different locations along the reference metaphase chromosomes wherein the greater the intensity of the signal at a location due to one subject DNA relative to the intensity of the signal due to the other subject DNA at that location, the greater the copy number of the sequence that binds at that location in the first subject cell or cell population relative to the copy number of the substantially identical sequence in the second subject cell or cell population that binds at that location.

Further disclosed are methods of quantitatively comparing copy numbers of different DNA sequences in one subject cell or cell population relative to copy numbers of substantially identical sequences in another subject cell or cell population. A representative method is that comprising steps (a) through (e) of the method immediately detailed above and the following steps of:

f. measuring the intensities of the signals from each of the bound subject DNAs and calculating the ratio of the intensities as a function of position along the reference metaphase chromosomes to form a ratio profile; and g. quantitatively comparing the ratio profile among different locations along the reference metaphase chromosomes, said ratio profile at each location being proportional to the ratio of the copy number of the DNA sequence that bind to that location in the first subject cell or cell population to the copy number of substantially identical sequences in the second cell or cell population.

Said representative methods can further comprise comparing copy numbers of different DNA sequences in more than two subject DNAs wherein the comparing is done pairwise between the signals from each subject DNA.

This invention further discloses methods to determine the ratio of copy numbers of different DNA sequences in one subject cell or cell population to copy numbers of substantially identical sequences in another cell or cell population wherein the steps of (a) through (f) as described above are performed as well as the following steps:

g. determining the average copy number of a calibration sequence in both subject cells or cell populations, said calibration sequence being substantially identical to a single copy sequence in the reference metaphase cells; and h. normalizing the ratio profile calculated in (f) so that at the calibration position, the ratio profile is equal to the ratio of the average copy numbers determined in (g), the normalized ratio profile at any other location along the reference metaphase chromosomes thereby giving the ratio of the copy numbers of the DNA sequences in the two subject DNAs that bind at that location. That method can be extended to further subject nucleic acids as for example determining the ratio of copy numbers of DNA sequences in more than two subject DNAs wherein the comparing is done pairwise between signals from each subject DNA.

Further disclosed are methods for comparing copy numbers of different DNA sequences in a test cell or cell population, said method comprising applying steps (a) through (e) of the above-described methods and f. observing and/or measuring the intensities of the signal from each subject DNA, and the relative intensities, as a function of position along the reference metaphase chromosomes wherein one of the subject cells or cell populations is the test cell or cell population and the other is a normal cell or cell population; and (g) comparing the relative intensities among different locations along the reference metaphase chromosomes, wherein the greater the relative intensity at a location, the greater the copy number of the sequence in the test cell or cell population that binds to that location, except for sex chromosomes where the comparison needs to take into account the differences in copy numbers of sequences in the sex chromosomes in relation to those on the autosomes in the normal subject cell or cell population.

A related representative method is that for comparing the copy number of different DNA sequences in a test cell or cell population comprising applying steps (a) through (e) of the above described methods wherein one of the subject cells or cell populations is the test cell or cell population, and the other is a standard cell or cell population wherein the copy numbers of the DNA sequences that bind to different positions on the reference metaphase chromosomes is known and steps:

f. measuring the intensities of the signals from each of the bound subject DNAs and calculating the ratio of intensities as a function of position along the reference metaphase chromosomes to form a ratio profile;

g. adjusting the ratio profile at each location along the reference metaphase chromosomes by multiplying the ratio profile by the known copy number of DNA sequences in the standard cell or cell population that bind there; and h. comparing the adjusted ratio profiles at different locations along the reference metaphase chromosomes wherein the greater the adjusted ratio profile at a location, the greater the copy number of the DNA sequence in the test cell or cell population that binds there.

Another related representative method is that for determining the ratios of the copy numbers of different DNA sequences in a test cell or cell population, said method comprising applying steps (a) through (f) of the immediately above-described method and the steps of adjusting the ratio profile at each location along the reference metaphase chromosomes by multiplying the ratio profile by the known copy number of sequences that bind there; and calculating the ratio of the copy number of a DNA sequence in the test cell or cell population that binds to one location on the reference metaphase chromosomes to the copy number of a sequence that binds to another location by dividing the adjusted ratio profile at the location of the first sequence by that at the location of the second. Said representative method can be extended to determine the copy number of different DNA sequences in a test cell or cell population wherein steps (a) through (f) as described above are followed and then the following steps of adjusting the ratio profile at each location along the reference metaphase chromosomes by multiplying the ratio profile by the known copy number of DNA sequences in the standard cell or cell population that bind there;

determining the copy number of a calibration sequence in the test cell or cell population that is substantially identical to a single copy sequence in the reference cells; and normalizing the adjusted ratio profile so that at the location of the calibration sequence on the reference metaphase chromosomes, the normalized, adjusted ratio profile is equal to the copy number of the calibration sequence determined in the above step, the value of the normalized, adjusted ratio profile at another location then being equal to the copy number of the DNA sequence in the test cell or cell population that binds at that location. That method can be analogously performed wherein two or more calibration sequences are used, and the adjusted ratio profile is normalized to get the best fit to the copy numbers of the ensemble of calibration sequences. Preferably, the copy number of the calibration sequence is determined by in situ hybridization. Those methods can comprise in situ hybridizing probes for more than one calibration position and normalizing to obtain the best fit of the ratio profile to the calibration positions. The standard cell or cell population preferably have normal genomes. In many applications of CGH, the reference metaphase chromosomes are normal.

Further, this invention concerns the use of antenna cell lines. An exemplary method is for detecting amplification of a certain sequence or group of sequences in a subject cell or cell population, comprising essentially steps (a) through (e) of the above-described methods wherein the in situ hybridization is targeted to antenna cells in which the DNA sequence(s) to be tested for is or are amplified, and examining the reference cell for regions that are hybridized significantly more intensely than others, the presence of such regions indicating amplifications of the sequence(s) which are being tested. The chromosomes of said antenna cell lines may be in interphase or in metaphase.

When a single labeled subject nucleic acid is being hybridized, or if multiple labeled subject nucleic acids are hybridized sequentially, it is important that the binding sites on the reference genome not be saturated prior to observing and/or measuring the signal intensity(ies). In the case of a single labeled subject nucleic acid, nonsaturation can be effected in a number of ways, for example, by stopping the hybridization, by providing insufficient subject nucleic acid, and/or by providing a sufficient amount of unlabeled nucleic acid which is sufficiently complementary to the reference chromosomes to competitively prevent saturation of sites therein by the labeled subject nucleic acid.

When there are two or more labeled subject nucleic acids, those subject nucleic acids can be hybridized in situ to the reference genome sequentially or simultaneously. Simultaneous in situ hybridization is preferred in that saturation of the targeted binding sites in the reference genome will not interfere with the procedure. When sequential in situ hybridization is used, it must be performed under conditions wherein the individual hybridizations are stopped well before the binding sites on the reference chromosomes are saturated.

Objects of this invention are to detect sequence copy number imbalances throughout an entire genome in one hybridization, to map gains and/or losses of sequences in a genome, and/or to provide a copy number karyotype of a subject genome.

Further, an object of this invention is to enable the detection of relative copy number differences that are common to a number of different cells and/or cell populations. For example, CGH methods can be used wherein DNAs extracted from cells of many different tumors are combined and labeled; the hybridization of those combined labeled DNAs to normal condensed chromosomes, provides for the rapid identification of only those copy number changes that occurred in most of the tumors. Less frequently occurring variations would be averaged out. Thus, this invention further provides for a CGH method wherein two or more of the subject nucleic acids that were extracted from different cells and/or from numbers of cells from different cell populations, are labeled the same, and hybridized to a reference spread under conditions wherein repetitive sequences are removed and/or suppressed and wherein sequence copy number differences that are common in said combined labeled nucleic acid sequences are determined.

Another object of this invention is to provide the means of cytogenetically analysing archived chromosomal material, that is, fixed material from, for example, biopsied tissue specimens, preferably cataloged and keyed to medical records of patients from whom the specimens were taken, and archaeological chromosomal material. Such chromosomal material cannot, of course, be karyotyped according to traditional means in that no live cells are present to culture and from which to prepare chromosomal spreads. However, the nucleic acid can be extracted therefrom and amplified by a polymerase chain reaction (PCR) procedure or by a non-PCR procedure and tested by the methods of this invention.

This invention further provides for a method to detect simultaneously an ensemble of amplifications and/or deletions in a tumor wherein the results can be used to determine the subsequent behavior of that tumor. Said determination is made by associating the patterns of amplifications and/or deletions in tumor cells with the behavior of that tumor. Such associations can be made by testing, for example, as indicated immediately above, DNA from archived tumor tissue keyed to medical records, or when fresh tumor specimens are tested by CGH and the patients are followed. Further, such associations can be made with CGH methods wherein there are more than one subject cell and/or cell population, for example, one or more tumors.

Another object of this invention is to provide a method of analyzing cells from a suspected lesion at an early stage of development. An advantage of the methods of this invention is that only a few cells are necessary for the analysis. The early detection of amplifications and/or deletions in cells from a lesion allow for early therapeutic intervention that can be tailored to the extent of, for example, invasiveness known to be associated with such genetic rearrangements. Further, such early detection provides a means to associate the progression of the cells with the genetic rearrangements therein detected by the methods of this invention.

Tumors can be karyotypically heterogeneous containing therein various populations of cells each having different types of genetic rearrangements. As indicated above tumor cells are difficult to culture, and it is not clear that cultured cells are-representative of the original tumor cell population. This invention provides the means to by-pass the culturing obstacle and allows genetic characterization of tumor cells and thus, of the heterogeneity of tumors by testing cells from different subregions thereof according to the methods of this invention. Bulk extraction of the nucleic acid from many cells of a tumor can also be used to test for consistent amplifications and/or deletions within a tumor.

It is another object of this invention to provide methods of detecting amplifications and/or deletions of nucleic acid sequences wherein certain cell lines termed herein "antenna cell lines", are used to enhance the sensitivity of the detection.

It is still further an object of this invention to provide methods of prenatal or perinatal analysis wherein the nucleic acid of the child's cells is extracted and tested according to the methods of this invention. In one embodiment of CGH, such material is human and hybridized to a normal human metaphase spread to detect whether any deletions and/or amplifications are therein present, for example, an extra copy of chromosome 21, diagnostic for Down syndrome. Test kits for performing CGH methods are also provided.

BRIEF DESCRIPTION OF THE FIGURES

The file of this patent contains at least one drawing executed in color. Copies of this patent with color drawings will be provided by the Patent and Trademark Office upon request and payment of the necessary fee.

Figure 1:
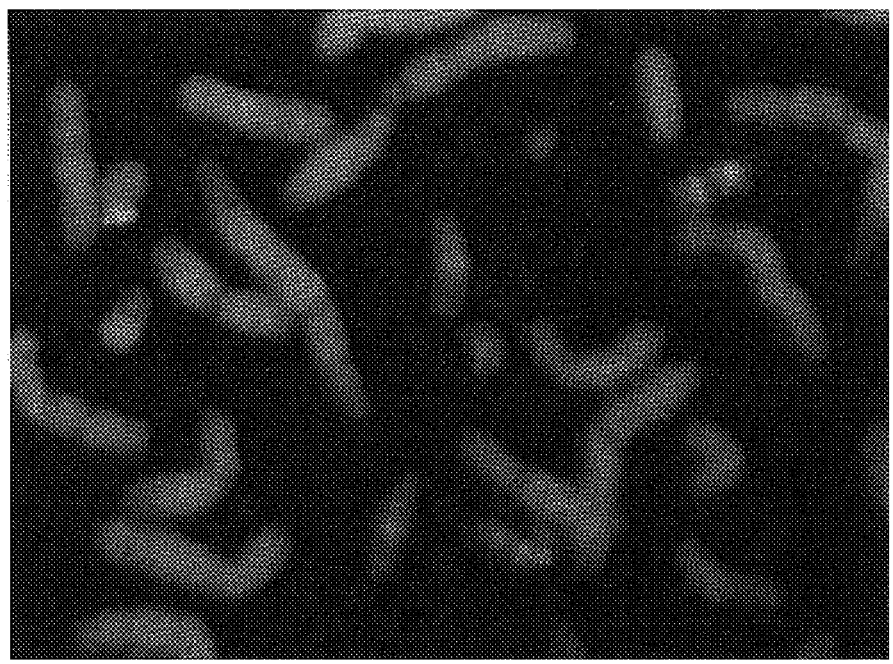
FIG. 1 illustrates the results of a CGH hybridization of DNA from the BT-474 human breast cancer cell line to a metaphase spread of normal peripheral blood lymphocyte human chromosomes. The BT-474 cell line is known to have a 13-fold c-erbB-2 amplification. The DNA from that cell line was labeled with digoxigenin-11-dUTP and stained with fluorescein isothiocyanate (FITC); signals from the hybridization of the cell line DNA are green in the photomicrograph. A chromosome 17 peri-centromeric repeat probe (cosmid cK17.10) was labeled with biotin-14-dATP and stained with Texas Red; signals from that probe's hybridization are red. The chromosomal DNA was counterstained with 4,6-diamidino-2-phenylindole (DAPI) resulting in a blue counterstaining. The photomicrograph was taken using a multicolor image analysis system after contrast stretching and pseudocolor display.

The green signals indicating amplified sequences in the BT-474 cell line are seen in FIG. 1 at the following loci: 17q12 (the erbB-2 locus), 17q22-q23 and 20q13-ter. The latter two sites were previously unrecognized sites of amplification in that cell line. One centromeric repeat is non-specifically stained green.

Figure 2:
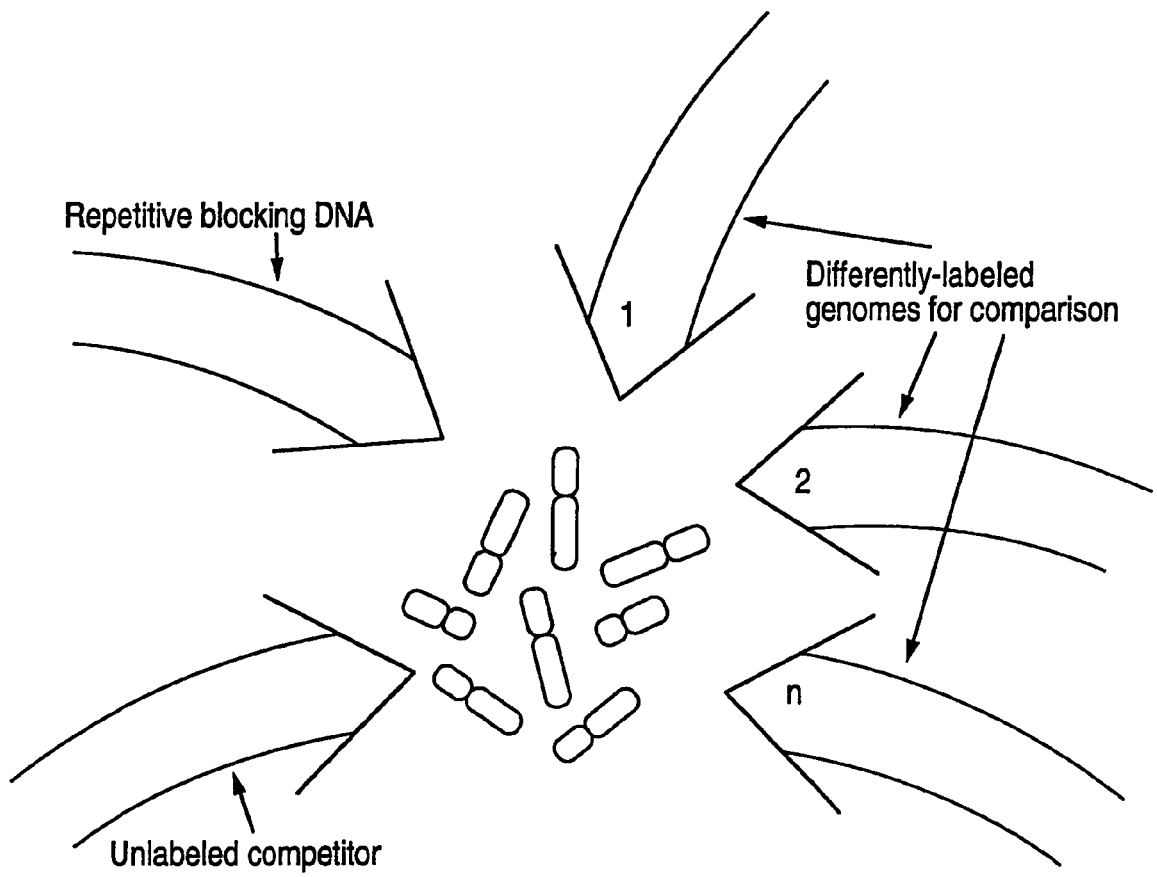

FIG. 2 schematically illustrates the general approach used in performing the methods of this invention—Comparative Genomic Hybridization (CGH). The reference chromosome spread is hybridized with various nucleic acid mixtures, either simultaneously or at different times, to obtain the desired information. Representative mixtures could include unlabeled sequences designed to block sequences in the various other nucleic acid pools, for example, the high-copy repetitive sequences in human genomic DNA; unlabeled competitor nucleic acid to prevent saturation of the target sites for the labeled mixtures, for example, human genomic DNA within a factor of 10 of the concentration used for the labeled subject nucleic acids (see FIG. 5); and one or more pools of sequences of different origin that are differently labeled so that their binding can be independently assessed, for example, tumor and normal genomic DNA (see FIGS. 6 and 7). The information on the sequence frequency of the labeled pools is obtained by analysis of the intensity of the individual signals and/or the differences in ratios of intensities among the signals as a function of position along the reference chromosomes.

Figure 3A:
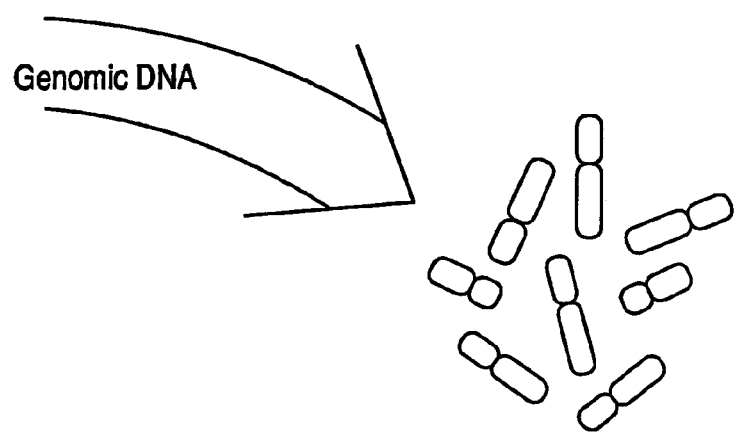
Figure 3B:
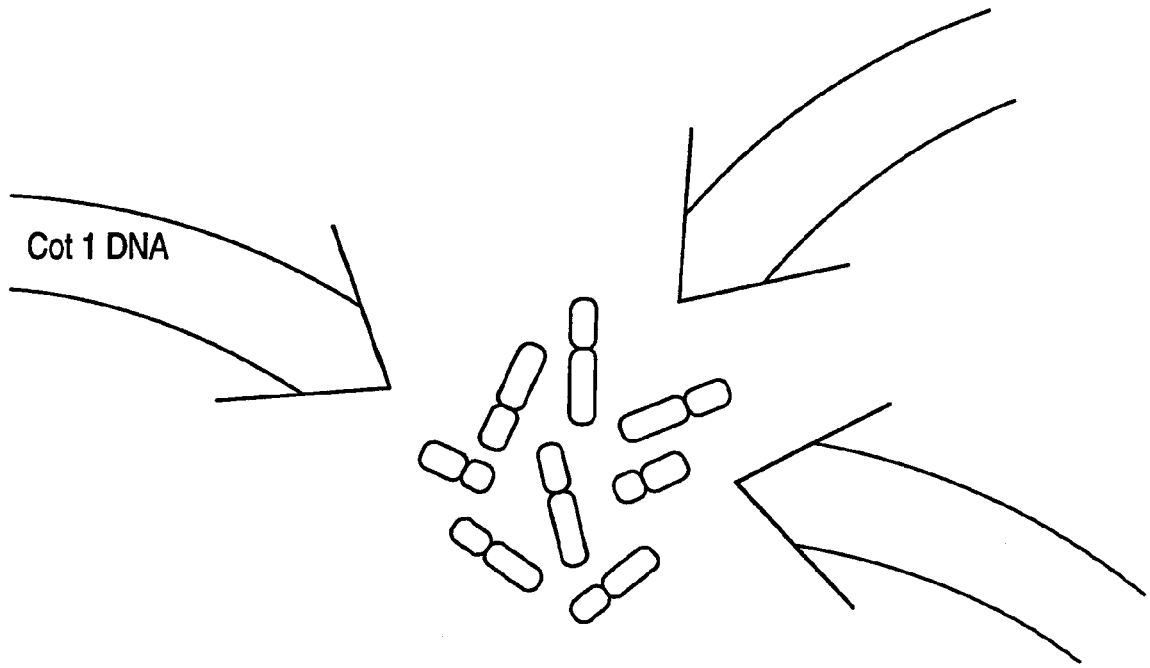

FIG. 3 outlines general aspects of the CGH procedure used in Example 1, infra. The reference chromosome spread, in this example normal human chromosomes, is first hybridized for about one hour with a high concentration of unlabeled human genomic DNA (FIG. 3a). That prehybridization blocks many of the high copy repetitive sequences in the chromosomes so that the high copy repetitive sequences in the labeled subject nucleic acid, in this case labeled tumor DNA, will not substantially contribute to the signal during the subsequent hybridization. The labeled tumor DNA, and perhaps some competitor DNA or other comparison nucleic acid are then hybridized to the target reference spread (FIG. 3b) Cot-1 DNA can be included in the hybridization as in Example 1, below to block more effectively the centromeric repetitive sequences in the labeled subject nucleic acids.

FIG. 3 is representative of one way of reducing signals from repetitive sequences. Other methods are detailed herein infra. In each of the CGH methods including the procedures outlined in the rest of the figures, some means of reducing the signal from the repetitive sequences is used, but not specifically indicated in the figures. It is important for CGH that the signal from each subject nucleic acid be dominated by sequences that bind to well-defined loci. Total suppression of the signal from the genomic repeats is not necessary, but the poorer the suppression, the less able the procedure is to detect small differences in sequence frequency.

Figure 4A:
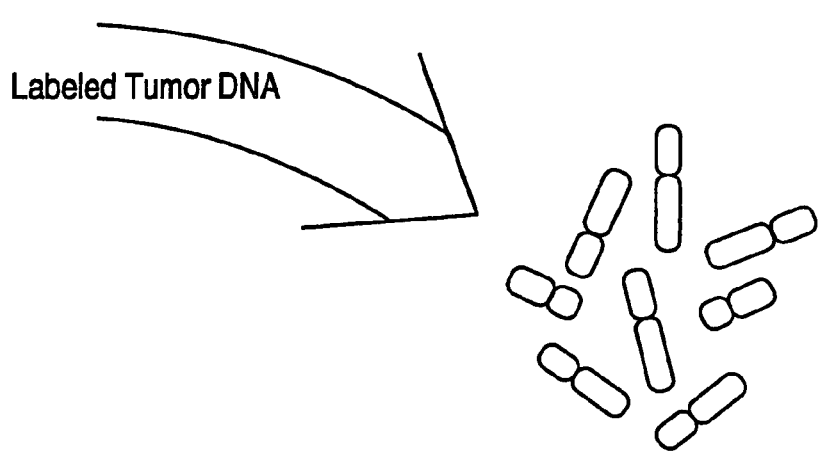
Figure 8:
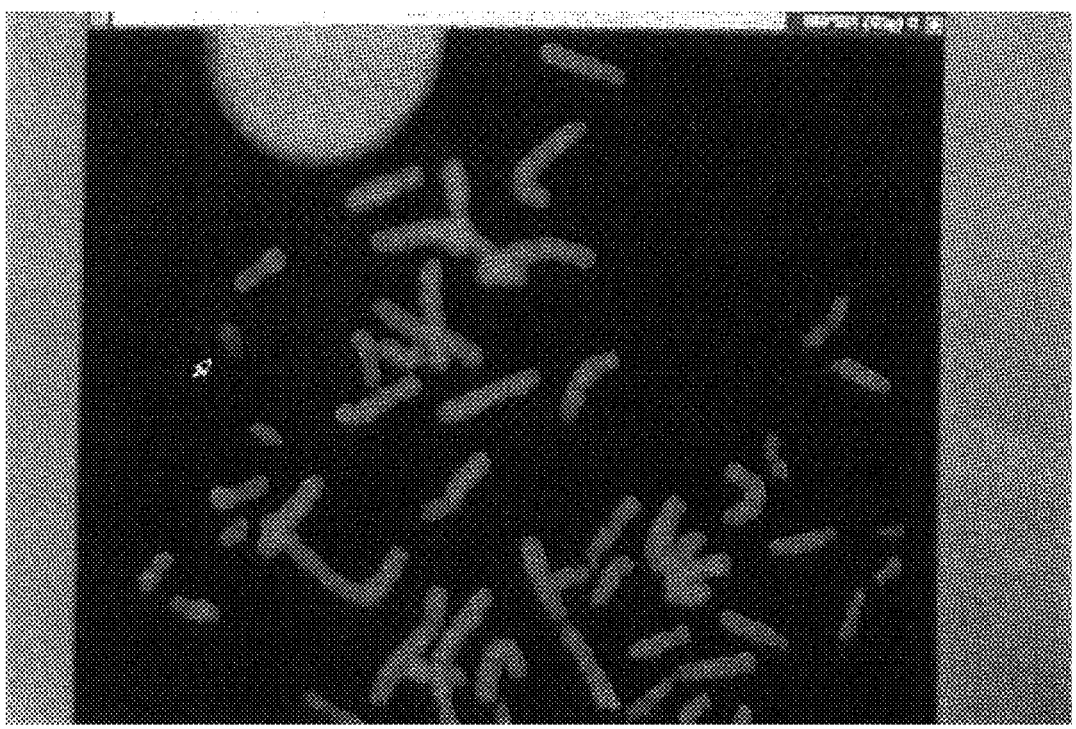

FIG. 4 illustrates the procedure used in Example 1, for which representative results are shown in the photomicrographs of FIGS. 1 and 8. As shown in FIG. 4a, labeled human tumor DNA is hybridized to a normal human chromosome spread. [Please note as indicated in the description for FIG. 3, provisions were made to suppress the signal from the repetitive sequences although those provisions are not specifically indicated in the figure. Example 1 details one preferred method to suppress the hybridization signals from repetitive sequences.] In this representative example, the tumor DNA is assumed to contain a region wherein some sequences are highly amplified, for example, an amplicon containing an oncogene. The amplified sequences in the tumor DNA may be clustered and integrated in some tumor chromosomes; they may be integrated into multiple places in the tumor genome; or, they may exist as extra-chromosomal elements. The sequences of the amplicon will map to some chromosomal location in the reference genome, which in this case is a normal human genome.

Figure 4B:
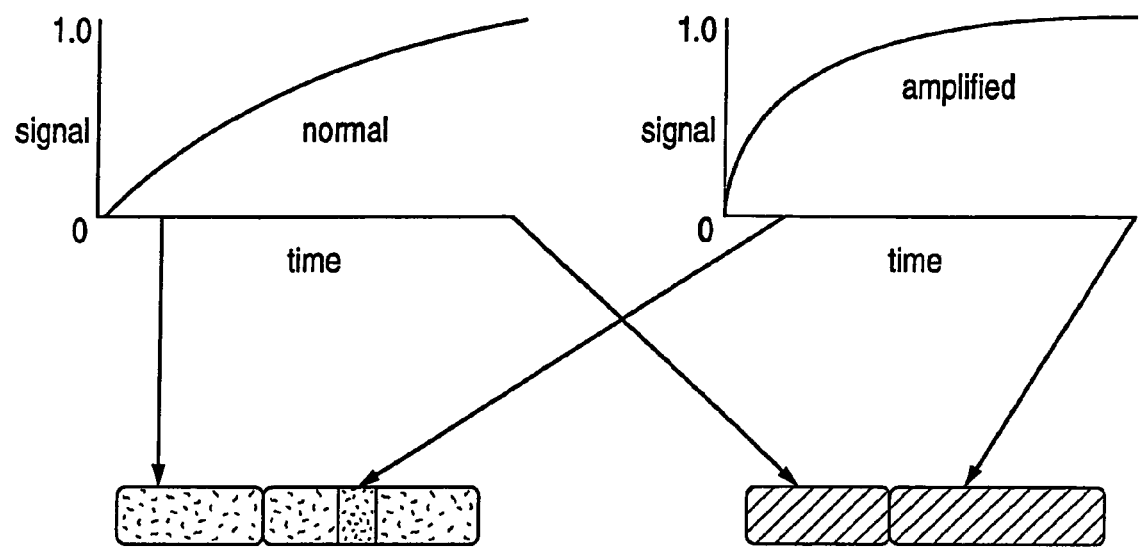

FIG. 4b illustrates the kinetics of the build-up of the signal on a target reference chromosome. The signal builds more rapidly in the amplified region since more copies of those sequences are available for hybridization. If the reaction is stopped before the target chromosome is saturated, or if insufficient labeled DNA is added to achieve saturation, then the genomic region that was amplified in the tumor will appear higher in intensity on the normal chromosome as illustrated by the dark band on the left reference chromosome. The more intensely labeled region (dark band) indicates the location and extent of the amplicon as reflected in the reference genome. Thus, the amplification is detected without prior knowledge of its existence, and the origin of the amplified sequences is mapped in the normal human genome.

If the reaction illustrated in FIG. 4b is allowed to proceed to saturation of the target sites, contrast is lost, as shown by the representative reference chromosome on the right. Thus, in this embodiment of CGH, it is important to stop the hybridization before saturation of the target or provide insufficient probe for saturation. The graphs schematically show the build-up of the hybridization signal in the region that was amplified (graph on right) and in the remainder that was unamplified (graph on the left). The arrows connect the chromosomal regions with the times of observation on the kinetic curve.

Figure 5A:
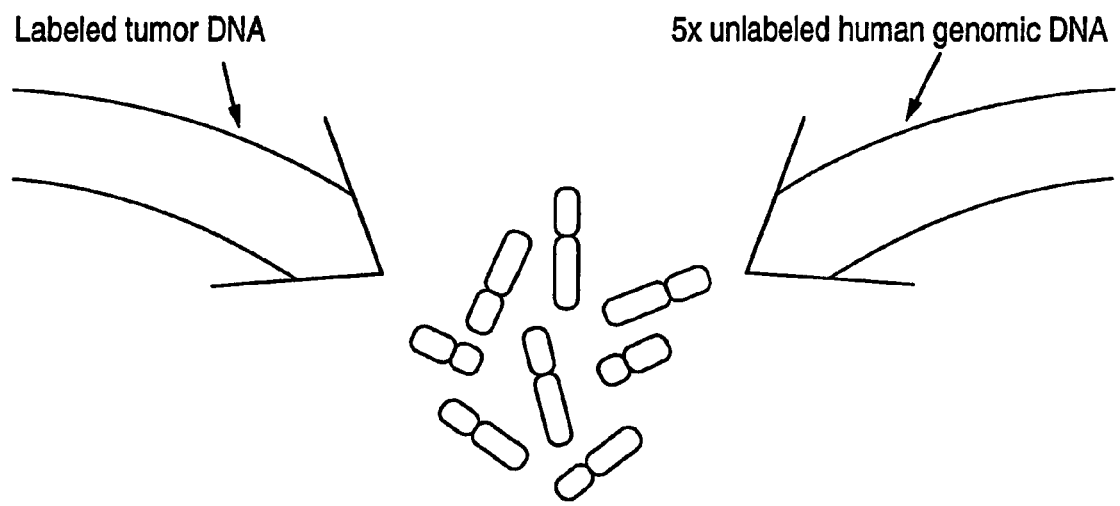
Figure 5B:
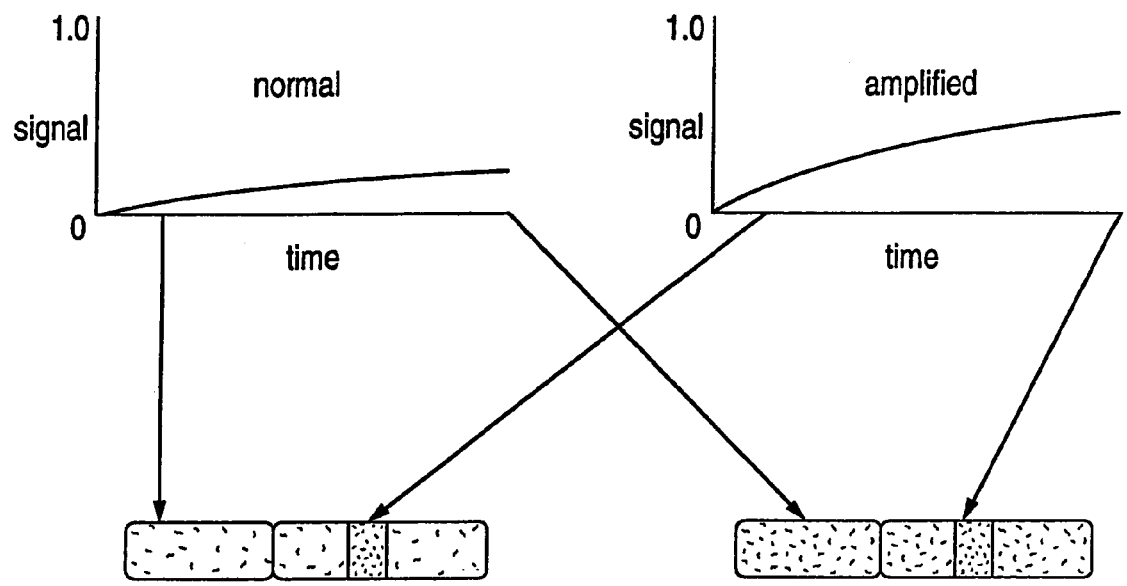

FIG. 5 illustrates an embodiment of CGH that avoids the potential saturation of the target as shown in the right portion of FIG. 4b. In this representative example, the reference nucleic acid is a human chromosome spread; the subject nucleic acid is labeled tumor DNA. If unlabeled human genomic DNA is included with the labeled tumor DNA in excess, in this case at a five-fold higher concentration than that of the labeled tumor DNA, then any saturation of the target will be due to a combination of labeled and unlabeled copies of the nucleic acid sequences, rather than just labeled copies as shown in the right of FIG. 4b. [Once again, as indicated in FIGS. 3 and 4 the means of reducing the signal from repetitive sequences is not indicated in this figure, but it is assumed that some protocol is performed to remove substantially the repetitive sequences that would bind to multiple loci in the reference genome and/or to block such sequences from binding to the target.]

At the early stages of the reaction, the amplified region will build up faster than elsewhere in the chromosome (for example if the sequence is amplified five-fold, it would build up 5 times as fast) and will be detectable as in the left portion of FIG. 4b. However as the reaction proceeds to saturation, the unamplified regions of the chromosome reach only one-fifth ($\frac{1}{5}$) of the intensity shown in FIG. 4b, because most of the sites are filled by unlabeled copies of the sequences. On the other hand, a sequence that was amplified five-fold in the tumor would reach one-half ($\frac{1}{2}$) of the saturation intensity since an equal number of labeled and unlabeled copies of those sequences are present. Thus, contrast is maintained according to this embodiment at all stages of the reaction, although it changes as the reaction proceeds.

Figure 6:
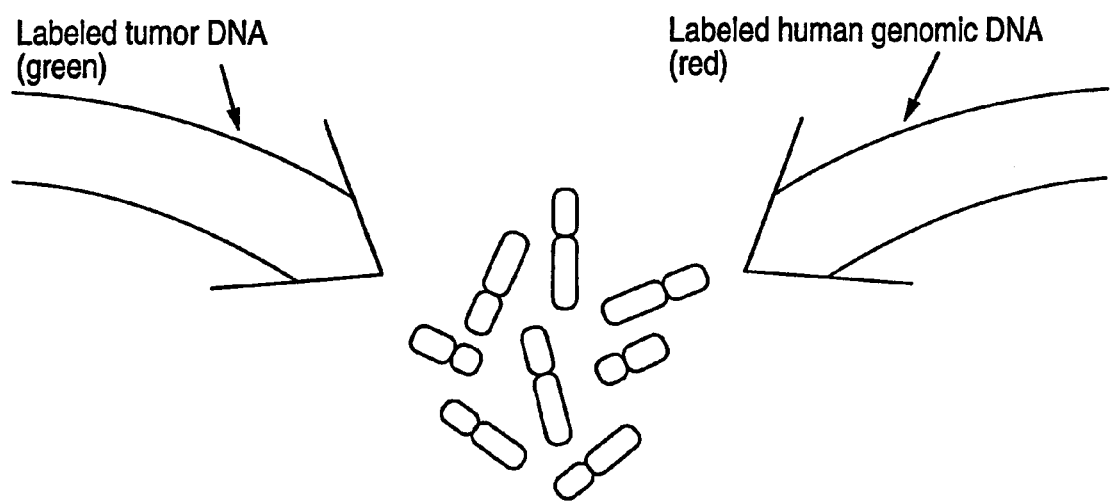

FIG. 6 illustrates an embodiment of CGH designed to enhance its sensitivity in detecting small changes in copy number of various sequences. When a CGH procedure as indicated in FIG. 5 is followed, intrinsic variation in the saturation levels, or rate of signal build-up at different positions in the reference genome may not be indicative of abnormal gain or loss of sequences. Such intrinsic variations would interfere with interpretation of intensity differences as indicating differences in copy number of the sequences. This CGH embodiment overcomes that potential problem by providing a mixture of labeled subject nucleic acid, in this case tumor DNA labeled with a green fluorochrome, and a differently labeled competitor nucleic acid in this case normal human genomic DNA labeled with a red fluorochrome. The two differently labeled DNAs are simultaneously hybridized to the chromosome spread. [Once again, removal of the repetitive sequences and/or blocking of the signal therefrom is performed but not illustrated.] Changes in the ratio of green to red along each of the chromosomes in the reference spread then indicate regions of increased or decreased sequence copy number in the tumor. Those ratio changes may result in color variations from red to yellow to green on the reference spread.

Figure 7:
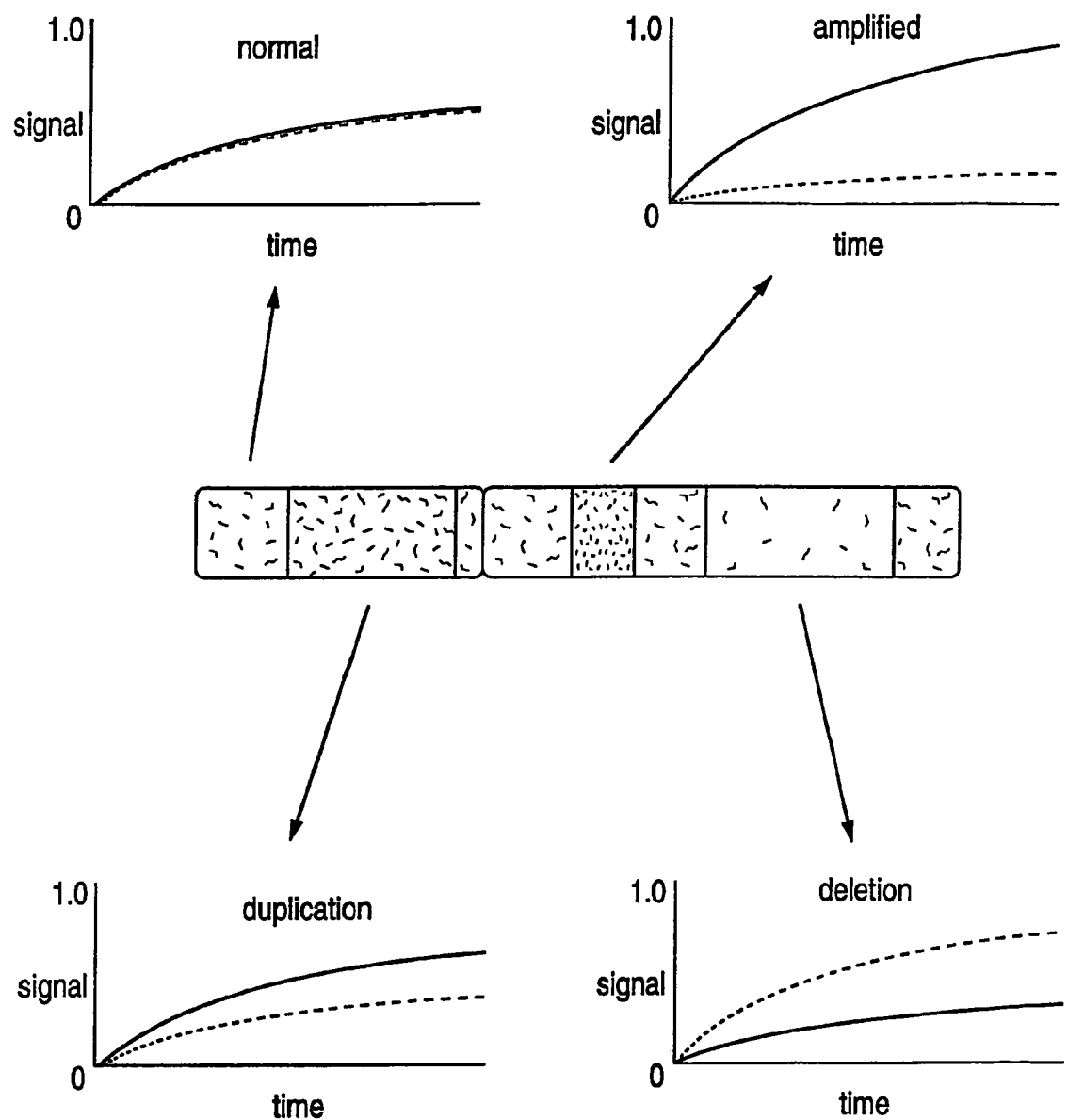

FIG. 7 graphically and schematically explains the kinetics underlying the CGH embodiment illustrated in FIG. 6. In the center is one of the chromosomes of the reference chromosome spread, a normal human chromosome in this case. The darkness of the shading on the reference chromosome shows the ratio of green to red intensity along the chromosome.

In the amplified region, the green/red ratio is much higher than in the normal region, whereas in the deleted region the green/red ratio is less than in the normal region. The arrows from examples of each of the different green/red intensity regions point to kinetic curves that indicate the build-up of green (solid line for the tumor DNA) and red (dashed line for the normal DNA) signals during the hybridization. In the normal region, upper left graph, the red and green signals build together. (They have been normalized to be equal for the purposes of this explanation.) In the amplified region, upper right, the green (tumor) signal builds up much more rapidly than the red (normal) signal, the green/red ratio being approximately the level of amplification (given the normalization to the normal part of the chromosome).

In the lower left of FIG. 7, the signal build-up for the duplicated region is shown; the green (tumor) signal is 50% brighter than the red (normal) signal. In the lower right, the build-up for a deleted region is schematically described; the green (tumor) signal is 50% dimmer than the red (normal) signal. The ratio approach of this CGH embodiment further normalizes for the frequent finding that hybridization to some chromosomes in a spread is intrinsically brighter than that for others because of differences in the local hybridization environment.

FIG. 8 illustrates an example of how a deletion can be detected using CGH. A deletion is simulated by employing DNA from a human primary breast carcinoma (XX) as a subject genome and a normal male chromosome spread (XY) as the reference genome. The absence of the Y-chromosome in the tumor DNA was detected, as would a cytogenetically significant deletion, by the hybridization. DNA from the primary breast carcinoma was labeled with digoxigenin-11-dUTP and stained with fluorescein isothiocyanate (FITC) (green signals). The normal male peripheral blood lymphocyte metaphase was counterstained with 4,6-diamidino-2-phenylindole (DAPI) (blue). The picture was taken from a multicolor image analysis system (QUIPS) after image thresholding and contrast stretching. The green chromosomal fluorescence level on all chromosomes was increased to make the absence of this fluorescence on the Y-chromosome (arrow) more readily visible. The Y-chromosome is only stained with the DAPI counterstain.

FIG. 9 presents an idiogram of chromosome 1 from the breast cancer cell line 600 MPE, the karyotype for which was published by Smith et al., *JNCI*, 78: 611-615 (1987).

Figure 10A:
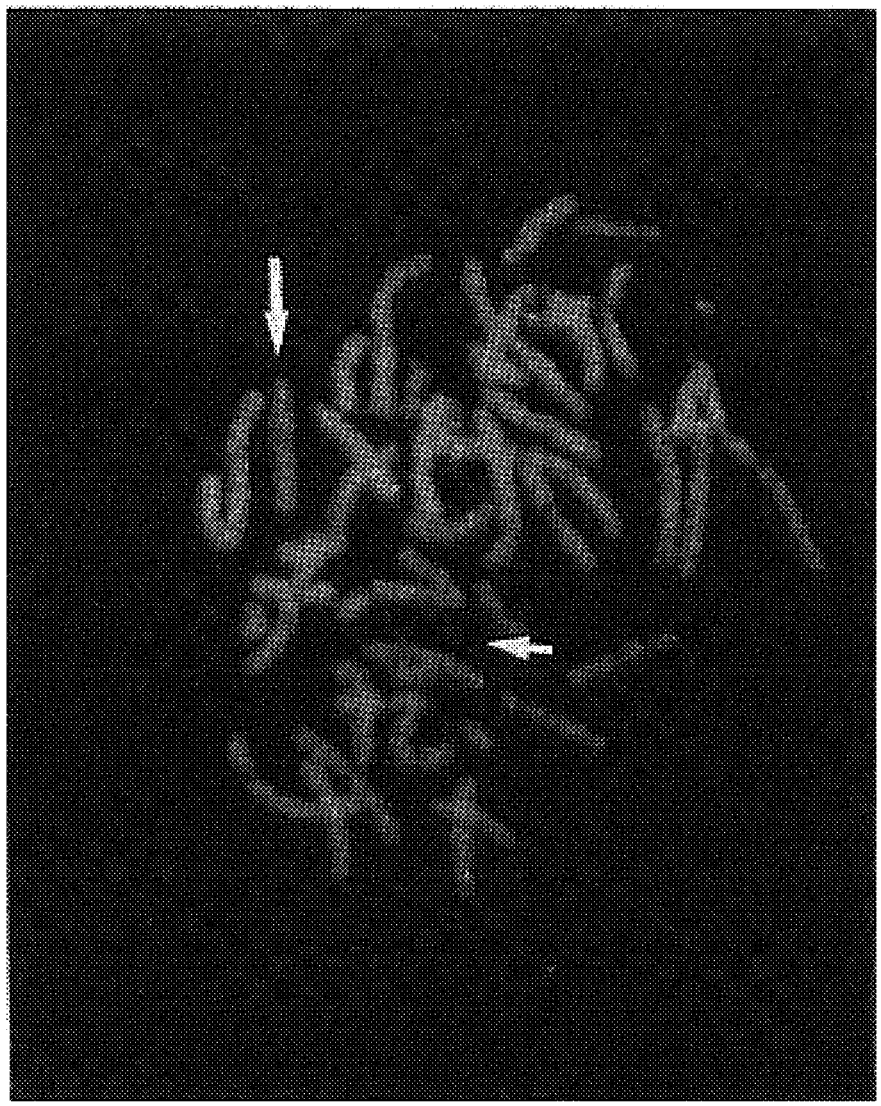
Figure 11A:
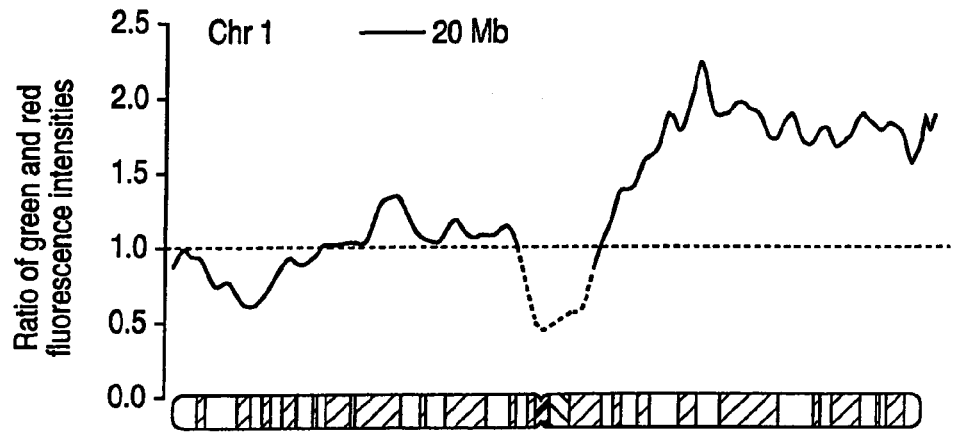
Figure 11B:
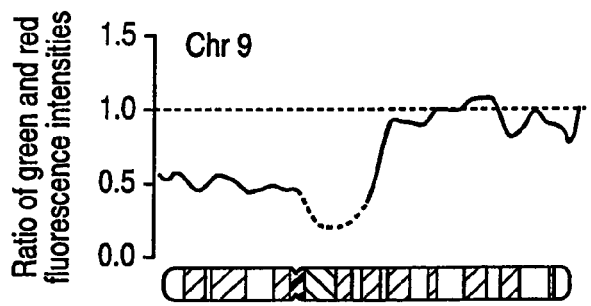
Figure 11C:
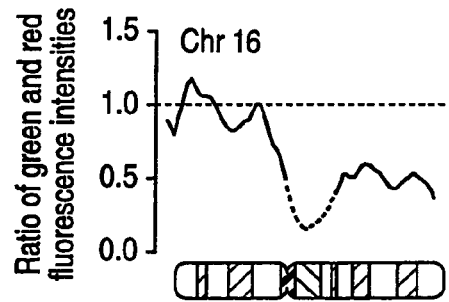
Figure 11D:
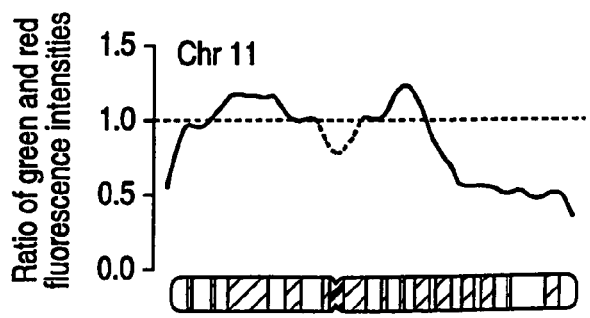
Figure 11E:
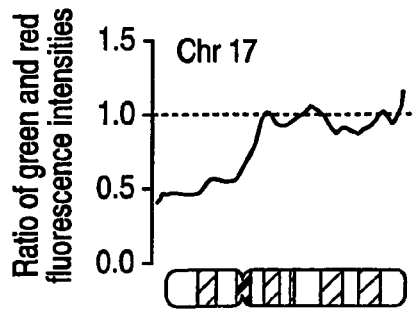

FIG. 10A is a photomicrograph showing the comparative genomic hybridization (CGH) of DNA from a 45, XO cell line (green) and a normal human female DNA (red) to a normal human male reference spread. The reddish color of the X chromosome, pointed out by the large arrow, as compared with the autosomes reflects the lower relative copy number of the X chromosome sequences in the 45, XO cell line. Faint staining of a small part of the Y chromosome, pointed out by the small arrow, is a result of the binding of homologous sequences in the pseudo-autosomal region.

FIG. 10B graphically illustrates the correlation of the number of X chromosomes in five fibroblast cell lines and the average green-to-red ratio of the X chromosome(s) relative to the same ratio for the autosomes.

FIGS. 11A-E illustrate green-to-red fluorescence ratio profiles of chromosomes 1, 9, 11, 16 and 17 after comparative genomic hybridization with breast cancer cell line 600PE (green) and with a normal DNA (red). The profiles reflect the relative copy number of the chromosomal regions. Fluorescence in situ hybridization (FISH) with 16p and 16q cosmid probes to interphase and metaphase 600PE cells indicated that there were two signals with 16p cosmid probes and one signal from the 16q cosmid probes. That information on the absolute copy number of those loci provided by FISH permits interpretation of the ratio 1.0 as indicating that there are two copies of the sequence throughout the genome.

The dip in the profile at 1p34 through 1p36 may represent a previously unsuspected small interstitial deletion; however, that observation has not yet been independently verified with specific probes for that region.

Centromeric and heterochromatic regions of the genome are not included in the analysis because the Cot-1 DNA partially blocks signals in those regions, and the large copy number polymorphisms between individual sequences at those loci effect unreliable ratio data.

Figure 12:
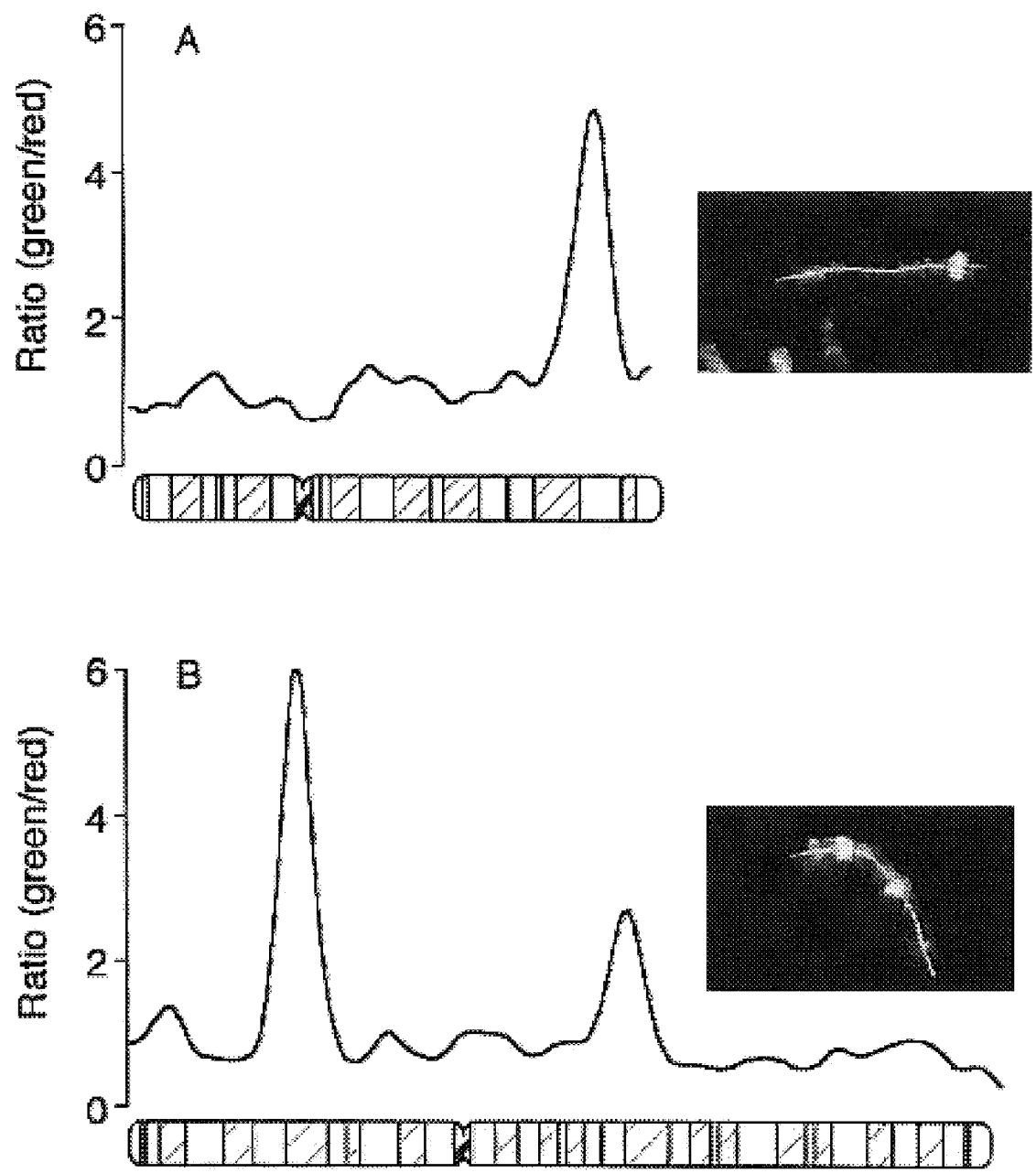

FIGS. 12(A) and 12(B) respectively provide green-to-red fluorescence ratio profiles of chromosome 8 (A) and chromosome 2 (B) after comparative genomic hybridization respectively with COLO 320 HSR (human colon adenocarcinoma cell line) and NCI H69 (small cell lung carcinoma cell line) cell line DNAs (green) and with normal human DNA (red). The inserts illustrate the overlaid green and red fluorescence images of the chromosomes, and the chromosomal medial axis drawn by the image analysis program used.

In FIG. 12(A), the myc locus at 8q24 shows a highly elevated green-to-red ratio, which is consistent with the known high level amplification of myc in the COLO 320HSR cell line.

In FIG. 12(B), three regions of amplification are seen on chromosome 2. The signal at 2p24 corresponds to the location of N-myc known to be amplified in the NCI-H69 cell line. The two other regions with a highly increased green-to-red fluorescence ratio, at 2p21 and 2q21, were not previously known to be amplified in the NCI-H69 cell line.

Figure 13:
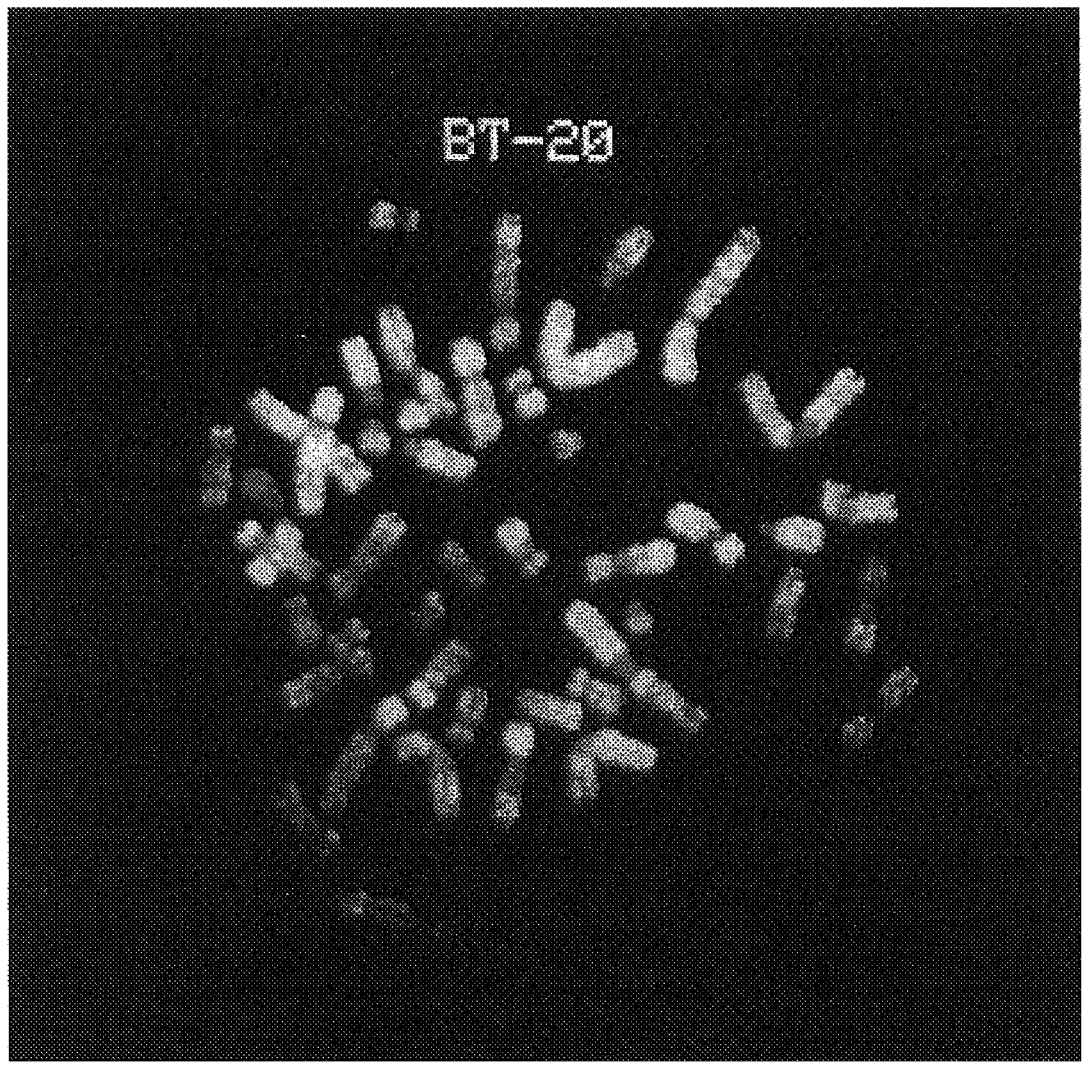

FIG. 13 is a photomicrograph of a comparative genomic hybridization (CGH) with BT-20 (breast cancer cell line) cell line DNA (green) and normal DNA (red) to a normal human metaphase spread. Loss of DNA sequences in the tumor cell line DNA relative to normal DNA are shown by red whereas gain of DNA sequences in the tumor cell line are shown in green.

DETAILED DESCRIPTION

Comparative Genomic Hybridization (CGH) has also been termed Copy Ratio Reverse Cytogenetics (CRRC), competition hybridization and quantitative in situ ratio karyotyping (QUIRK). Further, in the embodiment wherein fluorochromes are used as labels, it has been termed competition FISH (fluorescence in situ hybridization). CGH specifically provides methods whereby amplifications, duplications and/or deletions can be identified in an immediate overview of a genome.

CGH provides methods for determining variations in the copy number of different elements in a mixture of nucleic acid sequences (for example, genomic DNA isolated from a tumor) as a function of the location of those sequences in the genome of a reference organism (for example, the genome of a normal cell from the same species). The methods comprise the use of in situ hybridization of the nucleic acid sequence mixture to a chromosome spread of the reference organism, and measuring the intensity of the hybridization at different locations along the target chromosomes. Exemplary methods are schematically outlined in FIGS. 2-7. Those illustrative examples are not exhaustive but suggest the wide range of variations and other uses of the basic approach.

As the figure descriptions indicate, it is critical that signals from repetitive sequences do not dominate the signal from the subject nucleic acid pool, and that they be removed from the pool or that their signals be suppressed as necessary. It is preferred to exclude sequences from the hybridization or block sequences in the hybridization mixture that could bind to multiple clearly separated positions on the chromosomes, for example, sites that are on different chromosomes, or that are on the same chromosome but are well-separated. In many applications of CGH, it is the high copy repetitive sequences, such as Alu, Kpn, Lines, and alpha-satellites among others, that are removed from the labeled subject nucleic acid and/or which are blocked and/or the binding sites therefor are blocked. Described herein are methods to remove and/or block those repetitive signals. It should be noted that nucleic acid sequences in the labeled nucleic acid that bind to single copy loci are substantially retained in the hybridization mixture of labeled subject nucleic acids, and such single copy sequences as well as their binding sites in the reference chromosome spread remain substantially unblocked relative to the repetitive sequences that bind to multiple loci (that is, loci that are visually distinguishable) both before and during the hybridization.

The methods of this invention provide the means to identify previously unknown regions of amplification and deletion. For example, one embodiment of CGH as detailed in Example 1 herein provides an efficient method that gives an immediate overview of a genome identifying all regions that are amplified greater than about five-fold to ten-fold as well as at least large deletions. More sensitive embodiments that can identify smaller amplifications and deletions are also disclosed.

Nanogram quantities of the subject nucleic acids are required for the CGH methods of this invention. Paraffin embedded tumor sections can be used as well as fresh or frozen material. Snap frozen material from normal and malignant tissue are preferred for mRNA isolation.

Standard procedures can be used to isolate the required nucleic acid from the subject cells. However, if the nucleic acid, for example, DNA or mRNA, is to be extracted from a low number of cells (as from a particular tumor subregion) or from a single cell, it is necesary to amplify that nucleic acid, by a polymerase chain reaction (PCR) procedure or by a non-polymerase chain reaction (non-PCR) procedure. PCR and preferred PCR procedures are described infra. Exemplary non-PCR procedures include the ligase chain reaction (LCR) and linear amplification by use of appropriate primers and their extension (random priming).

Some of the various embodiments of CGH are illustrated, particularly in FIGS. 2-7. In the embodiment illustrated in FIGS. 6 and 7, wherein a subject nucleic acid, in this case, human genomic DNA, that is labeled differently from another subject nucleic acid, amplifications and/or deletions are indicated by a change in ratio between the different signals, rather than just a change in signal intensity.

The representative examples concerning CGH of Examples 1, 2 and 3 below involve the hybridizations of tumor cell line DNA to normal human metaphase spreads. However, there are many permutations and combinations of pairwise and multiple hybridizations of different nucleic acids from different genomes all of which are considered to be within the scope of this invention.

For example, CGH could be used to hybridize labeled DNA from a tumor cell line to metaphase spreads of that same cell line to estimate the level and pattern of amplification in each cell line, comparing those results to hybridizations of said tumor cell line DNA to a normal human metaphase spread. Alternatively, labeled tumor cell line DNA and differently labeled human genomic DNA could be simultaneously hybridized to a metaphase spread of a tumor cell line metaphase spread. Further, DNA from a primary tumor and that from its metastasis could be differently labeled and hybridized in a CGH method to a normal human metaphase or to a related tumor cell line metaphase. Those are just some of the many examples of CGH.

Although the examples herein concern the hybridizations of the DNA from breast cancer cell lines and primary tumors to normal human metaphase spreads, it will be clear to anyone skilled in the art that CGH is not limited to studying genomes of cancer cells or to the results of hybridizing abnormal genomes to normal genomes. CGH permits the comparison of nucleic acid sequence copy frequencies of any two or more genomes, even genomes of different species if their nucleic acid sequences are sufficiently complementary to allow for meaningful interpretation. It should be noted regarding interspecies comparisons that the information obtained by CGH includes not only an assessment of relative copy number but also that of sequence divergence.

It will also be clear to those skilled in the art that hybridization with nucleic acid other than chromosomal DNA, such as messenger RNA (mRNA) or complementary DNA (c-DNA) of subject cells can be used to determine the location and level of expression of genes in those cells. Conventional methodology is used to extract mRNA from a cell or cell population, and to synthesize in vitro c-DNA by reverse transcription.

CGH does not require the preparation of condensed chromosomes, for example, metaphase, prophase or other condensed chromosomal states, of the subject genomes. Thus, genomes from which metaphase, prophase or otherwise condensed chromosomal spreads are difficult, time-consuming or not possible to prepare at least in good quality, for example, genomes of tumor cells or fetal cells can be studied by CGH.

In CGH, labeled subject nucleic acids, for example, labeled tumor DNA, is hybridized to a reference genome, for example, a normal human metaphase spread, under conditions in which the signal from amplified, duplicated and/or deleted nucleic acid sequences from the labeled nucleic acid can be visualized with good contrast. Such visualization is accomplished by suppressing the hybridization of repetitive sequences that hind to multiple loci including the high copy interspersed and clustered repetitive sequences, such as, Alu, Kpn, Lines, alpha-satellites among others, using unlabeled total human genomic nucleic acid, preferably DNA, and/or the repeat-enriched (Cot-1) fraction of genomic DNA, and/or by removing such repetitive sequences from the hybridization mixture. In providing the detection sensitivity required, the extent of suppression of the hybridization of repetitive sequences and/or removal thereof can be adjusted to the extent necessary to provide adequate contrast to detect the differences in copy number being sought; for example, subtler copy number changes may require the suppression or removal of lower level repetitive sequences.

When combining more than one labeled nucleic acid in a hybridization mixture, the relative concentrations and/or labeling densities may be adjusted for various purposes. For example, when using visual observation or photography of the results, the individual color intensities need to be adjusted for optimum observability of changes in their relative intensities. Adjustments can also be made by selecting appropriate detection reagents (avidin, antibodies and the like), or by the design of the microscope filters among other parameters. When using quantitative image analysis, mathematical normalization can be used to compensate for general differences in the staining intensities of different colors.

The kinetics of the CGH hybridizations are complicated. Since the subject nucleic acids are frequently double stranded, complementary sequences will reassociate in the hybridiztion mix as well as hybridizing to the target. Such reassociation may result in a more rapid decrease in concentration of the high copy sequences than the low copy ones, thereby making the signal intensity variations on the reference chromosomes less pronounced than the copy differences in the original subject DNAs. In addition, non-specific binding of the labeled subject DNAs to the slide, coverslip, etc. may generally reduce the concentration of that labeled subject nucleic acid during the hybridization. Those skilled in the art will recognize numerous methods of optimizing the quantitative aspects of CGH, such as, mathematical correction of digital images, supplying freshly denatured subject DNA during the hybridization, and adding unlabeled genomic DNA in excess to dominate the reassociation rates.

The resolution of CGH is presently at a level that can be seen through a light microscope, as is traditional cytogenetic staining. Thus, if a small sequence in a subject nucleic acid is amplified, to be seen as a signal in a subject genome, it must be amplified enough times for its signal to be able to be visualized under a light microscope. For example, the locus for erbB-2 which is relatively small (very approximately, a few hundred kb), needs to be amplified at least greater than five times to be visually distinguishable under a light microscope when the CGH embodiment used in Example 1 is employed. On the other hand, if a large section of a chromosome is present at increased frequency in a subject nucleic acid, the signal from that region would show up in the reference genome at a much lower level of amplification.

The term "labeled" is herein used to indicate that there is some method to visualize nucleic acid fragments that are bound to the target, whether or not the fragments directly carry some modified constituent. A section infra entitled "Labeling the Nucleic Acid Fragments of the Subject Nucleic Acids" describes various means of directly labeling the probe and other labeling means by which the bound probe can be detected.

The phrase "antenna cell line" is herein used to indicate a reference genome that has one or more known significant genetic aberrations, for example, a cell line known to have an oncogene that is highly amplified, for example, in large homogeneously staining regions (HSRs). The amplified regions of that cell line would thus provide a much bigger target site than a normal chromosome spread. Thus, observation of the signal from such a large target site would be easier in that on average the signal would be brighter from amplified target sequences in the reference genome as provided by such an antenna cell line. A subject nucleic acid extracted from, for example, a number of tumor cells, could be tested by a CGH hybridization to such an antenna cell line to see if it also contained amplification(s) of the oncogene known to be amplified in the cell line.

When an antenna cell line is used as the reference genome, there are instances wherein it can be used in interphase rather than as a chromosome spread. For example, if one is checking to see if a certain oncogene is amplified or not in the subject nucleic acid, interphase CGH is sufficient. However, the maximum amount of information is provided when condensed chromosome spreads are used.

A base sequence at any point in the genome can be classified as either "single-copy" or "repetitive". For practical purposes the sequence needs to be long enough so that a complementary probe sequence can form a stable hybrid with the target sequence under the hybridization conditions being used. Such a length is typically in the range of several tens to hundreds of nucleotides.

A "single-copy sequence" is that wherein only one copy of the target nucleic acid sequence is present in the haploid genome. "Single-copy sequences" are also known in the art as "unique sequences". A probe complementary to a single-copy sequence has one binding site in haploid genome. A "repetitive sequence" is that wherein there is more than one copy of the same target nucleic acidisequence in the genome. Each copy of a repetitive sequence need not be identical to all the others. The important feature is that the sequence be sufficiently similar to the other members of the family of repetitive sequences such that under the hybridization conditions being used, the same fragment of probe nucleic acid is capable of forming stable hybrids with each copy.

Herein, the terms repetitive sequences, repeated sequences and repeats are used interchangeably.

The phrase "metaphase chromosomes" in herein defined to encompass the concept of "condensed chromosomes" and is defined to mean not only chromosomes condensed in the prophase or metaphase stage of mitosis but any condensed chromosomes, for example, those condensed by premature chromosome condensation or at any stage in the cell cycle wherein the chromosome can be visualized as an individual entity. It is preferred that the chromosomes in the reference genome be as long as possible but condensed sufficiently to be visualized individually.

A subject nucleic acid is herein considered to be the same as another nucleic acid if it is from a member of the same sex of the same species and has no significant cytogenetic differences from the other nucleic acid. For example, the DNA extracted from normal lymphocytes of a human female is considered for the purposes of this invention to be the same nucleic acid as that of DNA from normal cells of a human female placenta.

The following abbreviations are used herein:

| | Abbreviations |
|---|---|
| AAF | N-acetoxy-N-2-acetyl-aminofluorene |
| ATCC | American Type Culture Collection |
| BN | bicarbonate buffer with NP-40 |
| BRL | Bethesda Research Laboratories |
| bp | base pair |
| CCD | charge coupled device |
| CGH | Comparative Genomic Hybridization |
| Chr. | chromosomal |
| CML | chronic myelogenous leukemia |
| CRRC | Copy Ratio Reverse Cytogenetics |
| DAPI | 4,6-diamidino-2-phenylindole |
| dATP | deoxyadenosine triphosphate |
| DCS | as in fluorescein-avidin DCS (a commercially available cell sorter grade of fluorescein Avidin D) |
| dCTP | deoxycytosine triphosphate |
| dGTP | deoxyguanosine triphosphate |
| DI | DNA index |
| DM | double minute chromosome |
| dNTP | deoxynucleotide triphosphate |
| dTTP | deoxythymidine triphosphate |
| dUTP | deoxyuridine triphosphate |
| EDTA | ethylenediaminetetraacetate |
| E/P | estrogen/progesterone |
| FISH | fluorescence in situ hybridization |
| FACS | fluorescence-activated cell sorting |
| FITC | fluorescein isothiocyanate |
| HPLC | high performance liquid chromatography |
| HSR | homogeneously staining region |
| ISCN | International System for Cytogenetic Nomenclature |
| IB | isolation buffer |
| kb | kilobase |
| kDa | kilodalton |
| LOH | loss of heterozygosity |
| Mb | megabase |
| met. | metastasis |
| min | minute |
| ml | milliliter |
| mM | milliMole |
| mm | millimeter |
| ng | nanogram |
| NIGMS | National Institute of General Medical Sciences |
| NP-40 | non-ionic detergent commercially available from Sigma as Nonidet P-40 (St. Louis, MO) |
| PBS | phosphate-buffered saline |
| PCR | polymerase chain reaction |
| PHA | phytohemagglutinin |
| PI | propidium iodide |
| Pl. | pleural |
| PMSF | phenylmethylsulfonyl fluoride |
| PN buffer | mixture of 0.1 M $NaH_2PO_4$ and 0.1 M $Na_2HPO_4$, pH 8; 0.1% NP-40 |
| PNM buffer | Pn buffer plus 5% nonfat dry milk (centrifuged); 0.02% Na azide |
| QUIRK | quantitative in situ ratio karyotyping |
| Rb-1 | retinoblastoma tumor suppressor gene |
| RFLP | restriction fragment length polymorphism |
| RPM | revolutions per minute |
| SD | Standard Deviation |
| SDS | sodium dodecyl sulfate |
| SSC | 0.15 N NaCl/0.015 M Na citrate, pH 7 |
| Td | doubling time |
| ug | microgram |
| ul | microliter |
| um | micrometer |
| uM | micromole |
| VNTR | variable number tandem repeat |

Resolution of differences in copy number can be improved by the use of image analysis and by averaging the results from hybridizations of a subject nucleic acid to multiple condensed chromosome spreads. Using such methods, the background signal (noise) can be differentiated from actual nucleic acid sequence copy number differences.

Image Analysis:

An image analysis system, preferably computer-assisted, can be used to enhance and/or accurately quantitate the intensity differences between and/or among the signals from a hybridization and the background staining differences for more accurate and easier interpretation of results. Image analysis and methods to measure intensity are described, for example, in Hiraoka et al., *Science,* 238: 36-41 (1987) and Aikens et al., *Meth. Cell Biol.,* 29: 291-313 (1989). In such an image analysis system, it is preferred to use a high quality CCD camera whose intensity response is known to be linear over a wide range of intensities.

The components of a particular quantitative image processing system (QUIPS) are described in Example 1 under the subheading Fluorescence Microscopy and Interpretation of Results. As exemplified in Example 1, a computer-assisted image analysis system with a filterwheel is used so that the images from the signals and counterstaining of the DNA are superimposed on one image. Pseudocolors, that is, colors that are not exactly spectrally converted, can be displayed. Contrast stretching, wherein the differences between the intensity levels of the signals and background staining differences are enhanced by adjusting controls of the image analysis system. Thresholding can also be used wherein the background staining can be assigned a value close to zero so it would barely appear in the processed image from such a system. Similarly, computer analysis permits substraction of background, smoothing of fluctuations in the signals, accurate intensity and ratio calculations and the ability to average signals on chromosomes in multiple spreads.

Absolute Copy Numbers:

Hybridization of the subject DNAs to the reference chromosomes gives information on relative copy numbers of sequences. Some additional normalization is required to obtain absolute copy number information. One convenient method to do this is to hybridize a probe, for example a cosmid specific to some single locus in the normal haploid genome, to the interphase nuclei of the subject cell or cell population(s) (or those of an equivalent cell or representative cells therefrom, respectively). Counting the hybridization signals in a representative population of such nuclei gives the absolute sequence copy number at that location. Given that information at one locus, the intensity (ratio) information from the hybridization of the subject DNA(s) to the reference condensed chromosomes gives the absolute copy number over the rest of the genome. In practice, use of more than one reference locus may be desirable. In this case, the best fit of the intensity (ratio) data through the reference loci would give a more accurate determination of absolute sequence copy number over the rest of the genome.

Thus, the CGH methods of this invention combined with other well-known methods in the art can provide information on the absolute copy numbers of substantially all RNA or DNA sequences in subject cell(s) or cell population(s) as a function of the location of those sequences in a reference genome. For example, one or more chromosome-specific repeat sequence or high complexity painting probes can be hybridized independently to the interphase nuclei of cells representative of the genomic constitution of the subject cell(s) or cell population(s). Whole chromosome painting probes are now available for all the human chromosomes [Collins et al., *Genomics,* 11: 997-1006 (1991)]. Specific repeat-sequence probes are also available [Trask et al., *Hum.* *Genet.,* 78: 251 (1988) and references cited therein; and commercially available from Oncor (Gaithersburg, Md., USA)]. Hybridization with one or more of such probes indicates the absolute copy numbers of the sequences to which the probes bind.

For such interphase analysis, painting probes with a complexity of from about 35 kb to about 200 kb, are preferred; probes from about 35 kb to about 100 kb are further preferred; and still more preferred are probes having a complexity of from about 35 kb to 40 kb, for example, a cosmid probe. Exemplary of such locus-specific painting probes are any cosmid, yeast artificial chromosomes (YACs), bacterial artificial chromosomes (BACs), and/or p1 phage probes as appropriate, preferably to the arms of a selected chromosome. Such cosmid probes, for example, are commercially available from Clontech [South San Francisco, Calif. (USA)] which supplies cosmid libraries for all the human chromosomes. Another example of a cosmid probe that could be used in such methods of this invention would be a 3p cosmid probe called cC13-787 obtained from Yusuke Nakamura, M.D., Ph.D. [Division of Biochemistry, Cancer Institute, Toshima, Tokyo, 170, Japan]. Its isolation and mapping to 3p21.2-p21.1 is described in Yamakawa et al., *Genomics,* 9(3): 536-543 (1991). Another example would be a 3q cosmid probe named J14R1A12 obtained from Wen-Lin Kuo [Biomedical Department, P.O. Box 5507 (L-452), Lawrence Livermore National Laboratory Livermore, Calif. 94550 (USA)]. For interphase analysis, preferred repeat sequence probes are centromeric-specific and/or peri-centromeric-specific repeat sequence probes. Such a centromeric-probe is, for example, the chromosome 17 peri-centromeric repeat probe (cosmid ck17.10) and the alpha satellite repeat probe for the centromeric region of chromosome 8, both of which are described in Example 1 infra. A variety of repeat sequence probes are commercially available from Oncor [Gaithersburg, Md. (USA)]. However, the locus-specific painting probes are preferred over the repeat sequence probes for the methods of this invention to determine absolute copy numbers of nucleic acid sequences.

Further, when the subject nucleic acid sequences are DNA, the reference copy numbers can be determined by Southern analysis. When the subject nucleic acid sequences are RNA, the reference copy numbers can be determined by Northern analysis.

Those reference copy numbers or reference frequencies provide a standard by which substantially all the RNA or DNA sequences in the subject cell(s) or cell population(s) can be determined. CGH methods are used to determine the relative copy numbers of the rest of the sequences. However, absolute copy numbers require a standard against which the results of CGH can be determined. Otherwise the CGH procedures would have to be highly standardized and quantitated to see differences in the absolute copy numbers of sequences in a genome, for example, haploidy, triploidy, octaploidy, wherein there are 1, 3 and 8 copies of each of the chromosomes, respectively.

PCR and Microdissection:

The mechanics of PCR are explained in Saiki et al., *Science,* 230: 1350 (1985) and U.S. Pat. Nos. 4,683,195, 4,683, 202 (both issued Jul. 18, 1987) and 4,800,159 [issued Jan. 24, 1989).] PCR offers a rapid, sensitive and versatile cell-free molecular cloning system in which only minute amounts of starting material are required.

A preferred PCR method to amplify the subject nucleic acids for testing by CGH is a PCR adapter-linker amplification [Saunders et al., *Nuc. Acids Res.,* 17 9027 (1990); Johnson, *Genomics,* 6: 243 (1990) and PCT 90/00434 (published Aug. 9, 1990).] The labeled subject nucleic acid could be produced by such a adapter-linker PCR method from a few hundred cells; for example, wherein the subject nucleic acid is tumor DNA, the source DNA could be a few hundred tumor cells. Such a method could provide a means to analyse by CGH clonal sub-populations in a tumor.

Another preferred PCR method is a method employing a mixture of primers described in Meltzer et al., "Rapid Generation of Region Specific Probes by Chromosome Microdissection and their Application: A Novel Approach to Identify Cryptic Chromosomal Rearrangements," *Nature—Genetics.*, 1(1): 24-28 (April 1992). Microdissection of sites in the reference metaphase spread that produce signals of interest in CGH, would permit PCR amplification of nucleic acid sequences bound at such sites. The amplified nucleic acid could then be easily recovered and used to probe available libraries, as for example, cosmid libraries, so that the amplified sequences could be more rapidly identified.

High copy repetitive sequences can be suppressed in amplifying the subject nucleic acid by PCR. The PCR primers used for such a procedure are complementary to the ends of the repetitive sequences. Thus, upon proper orientation, amplification of the sequences flanked by the repeats occurs. One can further suppress production of repetitive sequences in such a PCR procedure by first hybridizing complementary sequences to said repetitive sequences wherein said complementary sequences have extended non-complementary flanking ends or are terminated in nucleotides which do not permit extension by the polymerase. The non-complementary ends of the blocking sequences prevent the blocking sequences from acting as a PCR primer during the PCR process. Primers directed against the Alu and L1 repetitive DNA families have allowed the selective amplification of human sequences by interspersed repetitive sequence PCR (IRS-PCR) [Nelson et al., *PNAS,* 86: 6686 (1989); Ledbetter et al., *Genomics,* 6: 475 (1990)].

Archived Material

An important aspect of this invention is that nucleic acids from archived tissue specimens, for example, paraffin-embedded or formalin-fixed pathology specimens, can be tested by the methods of CGH. Said nucleic acid cannot, of course, be prepared into chromosome spreads for traditional cytogenetic chemical staining. Also, it is difficult for large enough restriction fragments to be extracted from such material for other conventional research tools, such as Southern analysis. However, the nucleic acid from such specimens can be extracted by known techniques such as those described in Greer et al., *Anatomic Pathology,* 95(2): 117-124 (1991) and Dubeau et al., *Cancer Res.,* 46: 2964-2969 (1986), and if necessary, amplified for testing by various CGH methods. Such nucleic acid can be amplified by using a polymerase chain reaction (PCR) procedure (described above), for example, by the method described in Greer et al., supra wherein DNA from paraffin-embedded tissues is amplified by PCR.

A particular value of testing such archived nucleic acid is that such specimens are usually keyed to the medical records of the patients from whom the specimens were taken. Therefore, valuable diagnostic/prognostic associations can be made between the revealed cytogenetic state of patients' nucleic acid material and the medical histories of treatment and outcome for those patients. For example, information gathered by CGH can be used to predict the invasiveness of a tumor based upon its amplification and/or deletion pattern matched to associations made with similar patterns of patients whose outcomes are known.

Analogously, other nucleic acid that is fixed by some method, as, for example, archaelogical material preserved through natural fixation processes, can also be studied by CGH procedures. As indicated above, copy number differences between species provide information on the degree of similarity and divergence of the species studied. Evolutionarily important linkages and disjunctions between and among species, extant or extinct, can be made by using the methods of CGH.

Tumor Cytogenetics

CGH provides the means to assess the association between gene amplification and/or deletion and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as defined by CGH to, for example, normal metaphase spreads (genomic site, intensity of the signal and/or differences in signal ratios, and number of different genomic sites at which the copy number differences occur) can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by CGH could include atypical hyperplasia, ductal carcinoma in situ, stage I-III cancer and metastatic lymph nodes in order to permit the identification of associations between amplifications and deletions and stage.

The associations made may make possible effective therapeutic intervention. For example, consistently amplified regions may contain an overexpressed gene, the product of which may be able to be attacked therapeutically (for example, the growth factor receptor tyrosine kinase, $p185^{HER2}$).

CGH hybridizations of nucleic acids from cells of primary cancers that have metastasized to other sites can be used to identify amplification and/or deletion events that are associated with drug resistance. For example, the subject nucleic acids to be analysed could be selected so that approximately half are from patients whose metastatic disease responded to chemotherapy and half from patients whose tumors did not respond. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

Once a new region of amplification or deletion has been discovered by CGH, it can be studied in more detail using chromosome-specific painting [Pinkel et al., *PNAS (USA),* 85: 9138-9142 (1988); EP Publication No. 430,402 (Jun. 5, 1991)] with a collection of probes that span the amplified or deleted region. Probes to amplified regions. will show more signals than centromeric signals from the same chromosome, whereas probes to nonamplified regions will show approximately the same number of test and centromeric signals. For example, the amplified regions on 17q22-23 and 20qter (discussed as newly discovered regions of amplification in Example 1) show variability in size from tumor to tumor using CGH (the 17q22-23 region more markedly); it can be expected that the region containing the important gene(s) can be narrowed by mapping the regions of amplification in multiple tumors in more detail to find the portion that is amplified in all cases. Probes for those studies can be selected, for example from specific cosmid libraries produced by the National Laboratory Gene Library Project and/or from the National Institute of Health (NIH) genomic research projects.

The c-erbB-2 oncogene, also referred to as HER-2 or neu, encodes for a 185 kilodalton (Kd) protein. Studies have reported c-erbB-2 gene amplification in human mammary tumor cell lines. [Kraus et al., EMBO J. 6: 605-610 (1987); van de Vijver et al., Mol. Cell Biol., 7: 2019-2023 (1987).] Also, c-erbB-2 gene amplification in human breast cancer has been shown to be associated with disease behavior, and may be a predictor of clinical outcome. [Slamon et al., Science, 235: 177-182 (1987); Berger et al., Cancer Res., 48: 1238-1243 (1988); Zhou et al., Cancer Res., 47:6123-6125 (1987); and Venter et al., Lancet, 11: 69-71 (1987)]. C-erbB-2 has also been shown to be amplified in ovarian cancers. [Alitalo and Schwab, Advances in Cancer Res., 47: 235-281 (1986).]

C-myc is a proto-oncogene which is the cellular homolog of the transforming gene of the chicken retrovirus MC29. In humans, c-myc lies on the long arm of chromosome 8, at band 124, and spans about 5 kilobase pairs. The myc protein is a phosphoprotein present in the nucleus. The normal function of c-myc is unknown; however, it also certainly plays a role in cell division, and is expressed in normally growing cells as well as in tumor cells. It is now widely believed that translocations involving c-myc lead to altered transcription of the gene, contributing to malignant transformation.

Sequences from N-myc member of the myc gene family have been shown to be amplified as much as a thousandfold in some neuroblastomas. N-myc amplifications are usually seen in the later stage III and IV tumors. Some small-cell lung carcinomas also have amplified myc genes in double minute chromosomes (DMs) and homogeneously staining regions (HSRs). Mvc has also been shown to be amplified in colon cancer. [Alitalo and Schwab, supra.] Again such amplifications are found in late stages of tumor development, in the so-called variant cells that exhibit a more malignant behavior. Amplifications can involve either c-myc, N-myc or another member of the myc gene family, L-myc. [Watson et al., supra at pp. 1084-1086].

In addition, overexpression has been observed for the p-glycoprotein gene family associated with multi-drug resistance and for drug metabolizing enzymes such as P450 containing enzymes and glutathione S-transferase. [Fairchild and Cowan, J. Radiation Oncol. Biol. Phys., 20: 361-367 (1990).]

Identification of amplified and/or deleted genes is important to the management of cancer, for example breast cancer, for several reasons:

1) to improve prognostication;
2) to detect amplification and/or deletion events that are associated with the development of drug resistance; and
3) to improve therapy.

For example, in regard to improving prognostication, in breast cancer the amplification of oncogenes, such as int-2, erbB-2 and myc occur frequently and have been associated with aggressive growth and poor prognosis in some studies. [Schwab and Amier, Genes, Chromosomes & Cancer, 1: 181-193 (1990).] In regard to reason (2), gene amplification has clearly been shown to lead to drug resistance in vitro (for example, amplification of the dihydrofolate reductase gene confers resistance to methotrexate), and is likely to occur in patients undergoing therapy as well (for example, as a result of over expression of glutathione S-transferase and p-glycoprotein). [Fairchild and Cowan, supra]. Thus, the identification of resistance-linked genes would have a major impact on therapy by allowing therapy modification as resistance-related gene amplification occurs. Therapy could be improved by targeting for specific therapy, tumors that overexpress specific amplified genes.

Prenatal Diagnosis

Prenatal screening for disease-linked chromosome aberrations (e.g., trisomy 21) is enhanced by the rapid detection of such abberrations by the methods and compositions of this invention. CGH analysis is particularly significant for prenatal diagnosis in that it yields more rapid results than are available by cell culture methods.

Removal of Repetitive Sequences and/or Disabling the Hybridization Capacity of Repetitive Sequences The following methods can be used to remove repetitive sequences and/or disable the hybridization capacity of such repetitive sequences. Such methods are representative and are expressed schematically in terms of procedures well known to those of ordinary skill the art, and which can be modified and extended according to parameters and procedures well known to those in the art.

Bulk Procedures. In many genomes, such as the human genome, a major portion of distributed (or shared) repetitive DNA is contained in a few families of highly repeated sequences such as Alu. These methods primarily exploit the fact that the hybridization rate of complementary nucleic acid strands increases as their concentration increases. Thus, if a mixture of nucleic acid fragments is denatured and incubated under conditions that permit hybridization, the sequences present at high concentration will become double-stranded more rapidly than the others. The double-stranded nucleic acid can then be removed and the remainder used in the hybridizations. Alternatively, the partially hybridized mixture can be used as the subject nucleic acid, the double-stranded sequences being unable to bind to the target. The following are methods representative of bulk proceduresithat are useful for disabling the hybridization capacity of repetitive sequences or removing those sequences from a mixture.

Self-reassociation. Double-stranded nucleic acid in the hybridization mixture is denatured and then incubated under hybridization conditions for a time sufficient for the high-copy sequences in the mixture to become substantially double-stranded. The hybridization mixture is then applied to the reference chromosome spread. The remaining labeled single-stranded copies of the highly repeated sequences may bind throughout the reference chromosome spread producing a weak, widely distributed signal.

Use of blocking nucleic acid. Unlabeled nucleic acid sequences which are complementary to those sequences in the hybridization mixture whose hybridization capacity it is desired to inhibit are added to the hybridization mixture. The subject nucleic acids and blocking nucleic acid are denatured, if necessary, and incubated under appropriate hybridization conditions. The sequences to be blocked become double-stranded more rapidly than the others, and therefore are unable to bind to the reference spread when the hybridization mixture is applied to the spread. In some cases, the blocking reaction occurs so quickly that the incubation period can be very short, and adequate results can be obtained if the hybridization mix is applied to the spread immediately after denaturation. Further, the probe and the target can be simultaneously denatured in some cases. A blocking method is generally described in the context of Southern analysis by Sealy et al., "Removal of Repeat Sequences form Hybridization Probes", *Nucleic Acid Research*, 13:1905 (1985). Examples of blocking nucleic acids include genomic DNA, a high-copy fraction of genomic DNA and particular sequences as outlined below.

i. Genomic DNA. Genomic DNA contains all of the nucleic acid sequences of the organism in proportion to their copy-number in the genome. Thus, adding genomic DNA to the hybridization mixture increases the concentration of the high-copy repeat sequences more than low-copy sequences, and therefore is more effective at blocking the former.

ii. Hiah-copy fraction of aenomic DNA. Fractionating the genomic DNA to obtain only the high-copy sequences and using them for blocking can be done, for example, with hydroxyapatite as described below.

Removal of Sequences.

Hydroxyanatite. Single- and double-stranded nucleic acids have different binding characteristics to hydroxyapatite. Such characteristics provide a basis commonly used for fractionating nucleic acids. Hydroxyapatite is commerically available [e.g., Bio-Rad Laboratories, Richmond, Calif. (USA)]. The fraction of genomic DNA containing sequences with a particular degree of repetition, from the highest copy-number to single-copy, can be obtained by denaturing genomic DNA, allowing it to reassociate under appropriate conditions to a particular value of $C_o t$, followed by separation using hydroxyapatite. The single- and double-stranded nucleic acid can also be discriminated by use of S1 nuclease. Such techniques and the concept of $C_o t$ are explained in Britten et al., "Analysis of Repeating DNA Sequences by Reassociation", in *Methods in Enzymology*, 29: 363-418 (1974).

Reaction with immobilized nucleic acid. Removal of particular sequences can also be accomplished by attaching single-stranded "absorbing" nucleic acid sequences to a solid support. Single-stranded source nucleic acid is hybridized to the immobilized nucleic acid. After the hybridization, the unbound sequences are collected and used in CGH. For example, human genomic DNA can be used to absorb repetitive sequences from the subject nucleic acids. One such method is described by Brison et al., "General Method for Cloning Amplified DNA by Differential Screening with Genomic Probes," *Molecular and Cellular Biology*, 2: 578-587 (1982). Briefly, minimally sheared human genomic DNA is bound to diazonium cellulose or a like support. The source DNA, appropriately cut into fragments, is hybridized against the immobilized DNA to $C_o t$ values in the range of about 1 to 100. The preferred stringency of the hybridization conditions may vary depending on the base composition of the DNA.

Prehybridization. Blocking of repeat sequence binding sites in the reference genome by hybridization with unlabeled complementary sequences will prevent binding of labeled sequences in the subject nucleic acids that have the potential to bind to those sites. For example, hybridization with unlabeled genomic DNA will render the high-copy repetitive sequences in the reference genome double-stranded. Labeled copies of such sequences in the subject nucleic acids will not be able to bind when they are subsequently applied.

In practice, several mechanisms can be combined to produce the desired contrast and sensitivity.

Labeling the Nucleic Acid Fragments of the Subject Nucleic Acids

There are many techniques available for labeling single- and double-stranded nucleic acid fragments of the subject nucleic acids. They include incorporation of radioactive labels, e.g. Harper et al. *Chromosoma*, 83: 431-439 (1984); direct attachment of fluorochromes or enzymes, e.g. Smith et al., *Nuc. Acids Res.*, 13: 2399-2412 (1985), and Connolly et al., *Nuc. Acids Res.*, 13: 4485-4502 (1985); and various chemical modifications of the nucleic acid fragments that render them detectable immunochemically or by other affinity reactions, e.g. Tchen et al., "Chemically Modified Nucleic Acids as Immunodetectable Probes in Hybridization Experiments," *PNAS*, 81: 3466-3470 (1984); Richardson et al., "Biotin and Fluorescent Labeling of RNA Using T4 RNA Ligase," *Nuc. Acids Res.*, 11: 6167-6184 (1983); Langer et al., "Enzymatic Synthesis of Biotin-Labeled Polynucleotides: Novel Nucleic Acid Affinity Probes," *PNAS*, 78: 6633-6637 (1981); Brigati et al., "Detection of Viral Genomes in Cultured Cells and Paraffin-Embedded Tissue Sections Using Biotin-Labeled Hybridization Probes," *Virol.*, 126: 32-50 (1983); Broker et al., "Electron Microscopic Visualization of tRNA Genes with Ferritin-Avidin: Biotin Labels," *Nuc. Acids Res.*, 5: 363-384 (1978); Bayer et al., "The Use of the Avidin Biotin Complex as a Tool in Molecular Biology," *Methods of Biochem. Analysis*, 26: 1-45 (1980); Kuhlmann, *Immunoenzyme Techniques in Cytochemistry* (Weinheim, Basel, 1984). Langer-Safer et al., *PNAS* (USA), 79: 4381 (1982): Landegent et al., *Exp. Cell Res.*, 153: 61 (1984); and Hopman et al., *Exp. Cell Res.*, 169: 357 (1987). Thus, as indicated, a wide variety of direct and/or indirect means are available to enable visualization of the subject nucleic sequences that have hybridized to the reference genome. Suitable visualizing means include various ligands, radionuclides, fluorochromes and other fluorescers, chemiluminescers, enzyme substates or co-factors, particles, dyes and the like. Some preferred exemplary labeling means include those wherein the probe fragments are biotinylated, modified with N-acetoxy-N-2-acetylaminofluorene, modified with fluorescein isothiocyanate or other fluorochromes, modified with mercury/TNP ligand, sulfonated, digoxigeninated or contain T-T dimers.

A preferred method of labeling is tailing by terminal transferase labeling. Another preferred method is random priming with mixed sequence primers followed by polymerase extension. This has the additional feature of amplifying the amount of subject DNA, if several cycles are used, which is useful when only a small amount of DNA was originally obtained from the subject cell or cell population.

The key feature of labeling is that the subject nucleic acid fragments bound to the reference spread be detectable. In some cases, an intrinsic feature of the subject nucleic acid, rather than an added feature, can be exploited for this purpose. For example, antibodies that specifically recognize RNA/DNA duplexes have been demonstrated to have the ability to recognize probes made from RNA that are bound to DNA targets [Rudkin and Stollar, *Nature*, 265:472-473 (1977)]. The RNA used is unmodified. Nucleic acid fragments can be extended by adding "tails" of modified nucleotides or particular normal nucleotides. When a normal nucleotide tail is used, a second hybridization with nucleic acid complementary to the tail and containing fluorochromes, enzymes, radioactivity, modified bases, among other labeling means, allows detection of the bound nucleic acid fragments. Such a system is commercially available from Enzo Biochem [Biobridge Labeling System; Enzo Biochem Inc., New York, N.Y. (USA)].

Another example of a means to visualize the bound nucleic acid fragments wherein the nucleic acid sequences do not directly carry some modified constituent is the use of antibodies to thymidine dimers. Nakane et al., *ACTA Histochem. Cytochem.*, 20 (2):229 (1987), illustrate such a method wherein thymine-thymine dimerized DNA (T-T DNA) was used as a marker for in situ hybridization. The hybridized T-T DNA was detected immunohistochemically using rabbit anti-T-T DNA antibody.

All of the labeling techniques disclosed in the above references may be preferred under particular circumstances. Further, any labeling techniques known to those in the art would be useful to label the subject nucleic acids in of this invention. Several factors govern the choice of labeling means, including the effect of the label on the rate of hybridization and binding of the nucleic acid fragments to the chromosomal DNA, the accessibility of the bound nucleic acid fragments to labeling moieties applied after initial hybridization, the mutual compatibility of the labeling moieties, the nature and intensity of the signal generated by the label, the expense and ease in which the label is applied, and the like.

Several different subject nucleic acids, each labeled by a different method, can be used simultaneously. The binding of different nucleic acids can thereby be distinguished, for example, by different colors.

In Situ Hybridization.

Application of the subject nucleic acids to the reference chromosome spreads is accomplished by standard in situ hybridization techniques. Several excellent guides to the technique are available, e.g., Gall and Pardue, "Nucleic Acid Hybridization in Cytological Preparations," *Methods in Enzymology*, 21: 470-480 (1981); Henderson, "Cytological Hybridization to Mammalian Chromosomes," *International Review of Cytology*, 76: 1-46 (1982); and Angerer et al., "in situ Hybridization to Cellular RNAs," in *Genetic Engineering: Principles and Methods*, Setlow and Hollaender, Eds., Vol. 7, pgs. 43-65 (Plenum Press, New York, 1985).

Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagents used in each of these steps and their conditions of use vary depending on the particular situation.

Under the conditions of hybridization wherein human genomic DNA is used as an agent to block the hybridization capacity of the repetitive sequences, the preferred size range of the nucleic acid fragments is from about 200 bases to about 1000 bases, more preferably about 400 to 800 bases for double-stranded, nick-translated nucleic acids and about 200 to 600 bases for single-stranded or PCR adapter-linker amplified nucleic acids.

Example 1 provides details of a preferred hybridization protocol. Basically the same hybridization protocols as used for chromosome-specific painting as described in Pinkel et al., *PNAS (USA)*, 85: 9138-9142 (1988) and in EP Pub. No. 430,402 (published Jun. 5, 1991) are adapted for use in CGH.

The following representative examples of performing CGH methods of this invention are for purposes of illustration only and are not meant to limit the invention in any way.

EXAMPLE 1

DNA from Breast Cancer Lines Hybridized to Normal Metaphase Spreads

In this Example, methods of this invention to analyse genomes by Comparative Genomic Hybridization (CGH) are exemplified by hybridizations of breast cancer cell lines to normal metaphase spreads. The target metaphase spreads were pre-hybridized with unlabeled human placental DNA to block the high copy repeat sequences. In this representative example, the hybridization mixture containing the extracted labeled DNA from the cell lines contained unlabeled, repeat-enriched Cot-1 blocking DNA [obtained from Bethesda Research Laboratories (BRL), Gaithersburg, Md. (USA].

The experiments outlined below include in the hybridization mixture for the subject genomes, that is, the breast cancer cell line DNAs, chromosome-specific repeat sequence probes and chromosome-specific painting probes. Those probes labeled with biotin were included as an adjunct for identifying chromosomes in the metaphase preparations. The experiments were first performed without those chromosome-specific probes. Then each chromosome of interest was measured to determine its length which was considered along with other factors to determine its probable identity. The chromosome-specific probes were then used in the hybridization mixture to confirm the identity of the chromosome of interest. However, such probes are not necessary as the chromosomes could have been identified by the DAPI banding of the counterstain or by other chemical staining, such as staining with quinacrine, by a skilled cytogeneticist.

Cell Lines and Isolation of DNA:

Six established breast cancer cell lines: BT-474, SK-BR-3, MCF-7, MDA-MB-361, MDA-MB-468 and T-47D were obtained from the American Type Culture Collection [Rockville, Md. (USA)]. The breast cancer cell line 600MPE cell line was kindly provided by Dr. Helene S. Smith [Geraldine Brush Cancer Research Center, San Francisco, Calif. (USA)]. Cell lines were grown until they became confluent. Cells were then trypsinized, pelleted by centrifugation at 1500 RPM for 5 minutes and washed twice in phosphate buffered saline. The DNA was then isolated as described by Sambrook et al., *Molecular Cloning: A Laboratory Manual*, Vol. 2: 9.16-9.19 [Cold Spring Harbor Laboratory Press, Cold Spring Harbor, N.Y. (USA) 1989].

Details concerning the established human breast cancer cell lines used herein are as follows:

| | |
|---|---|
| BT-474 | Originated from a human primary cancer; obtained from the ATCC, catalog # HTB 20; |
| SK-BR-3 | Originated from a human metastatic breast adenocarcinoma derived from a pleural effusion; obtained from the ATCC catalog # HTB 30; |
| MDA-MB-361 | Originated as a metastatic tumor to the brain; obtained from the ATCC, catalog # HTB 27; |
| MCF-7 | Originated from a human metastatic pleural effusion; obtained from the ATCC, catalog # HTB 22; |
| T-47D | Originated as a human metastatic pleural effusion; obtained from the ATCC catalog # HTB 133; |
| 600MPE | Originated as a human metastatic pleural effusion; kindly provided by Dr. Helene S. Smith [Geraldine Brush Cancer Research Center, San Francisco, CA (USA)]; and |

| | |
|---|---|
| MDA-HB-468 | Originated as a metastatic pleural effusion; obtained from the ATCC, catalog # HTB 132. |

Preparation of Normal Lymphocyte Metaphases:

Normal peripheral blood lymphocytes were stimulated by PHA, synchronized by methotrexate treatment and blocked in metaphase using 0.05 ug/ml colcemid. Cells were then centrifuged, washed and incubated in 75 mM KCl at 37° C. for 15 minutes. Cells were then fixed in methanol:acetic acid (3:1) and dropped onto slides. The slides were stored under nitrogen at −20° C.

DNA Labeling:

Cell line DNAs were labeled with digoxigenin-11-dUTP using nick translation [Rigby et al., *J. Mol. Biol.*, 113: 237 (1977); Sambrook et al., supra]. The optimal size of the probe fragments after nick translation and before denaturing was 400-800 bps. As indicated above, chromosome-specific probes were used in dual-color hybridizations to verify the identification of chromosomes of interest in the metaphase spreads. Representative examples of such chromosome-specific reference probes labeled with biotin-14-dATP include the following:

1) a chromosome-specific painting probe for chromosome 20 prepared by the PCR adapter-linker method as described in PCT/US90/00434 published Aug. 9, 1990;

2) a chromosome 17 peri-centromeric repeat probe (cosmid ck17.10) isolated by Anne Kallioniemi from a chromosome 17 cosmid library from Los Alamos National Laboratory [Albuquerque, N.Mex. (USA)]; an equivalent chromosome-specific repeat sequence probe for chromosome 17 is commercially available from Oncor [Gaithersburg, Md. (USA)]; and 3) an alpha satellite repeat probe specific for the centromeric region of chromosome 8 [kindly provided by Dr. Heinz-Ulrich G. Weier; University of California Medical Center, Lab for Cell Analysis, San Francisco, Calif. (USA)]; that probe was generated by Dr. Weier using PCR with primers WA1 and WA2 as described in Weier et al., *Hum. Genet.*, 87: 489-494 (1991).

Ones skilled in the art recognize that there are many other equivalent probes available that could be used for the confirmation purposes described. For example, whole chromosome painting probes are now available for all the human chromosomes [Collins et al., *Genomics*, 11: 997-1006 (1991)]. Also available are repeat sequence probes that hybridize intensely and specifically to selected chromosomes [Trask et al., *Hum. Genet.*, 78: 251 (1988) and references cited therein].

Pretreatment and Prehybridization of Slides:

Lymphocyte metaphase preparations were first denatured in 70% formamide/2×SSC (1×SSC is 0.15 M NaCl, 0.015 M NaCitrate), pH 7, at 70° C. for 2 minutes and dehydrated in a sequence of 70%, 85% and 100% ethanol. The slides were then air dried and treated with 10 ug/50 ml Proteinase K [Boehringer Mannheim GmbH, Indianapolis Ind. (USA)] for 7.5 minutes at 37° C. in a buffer containing 20 mM Tris and 2 mM $CaCl_2$ (pH 7.5). Ethanol dehydration was then done as described above, and the slides were prehybridized with ten ul of a hybridization mixture, consisting of 20 ug unlabeled human placental DNA [obtained from Sigma, St. Louis, Mo. (USA); size of the fragments is 200-700 bps] in 50% formamide, 10% dextran sulphate and 2×SSC (pH 7) for 60 minutes at 37° C. Before the prehybridization mixture was applied to the slides, it was denatured in a 70° C. water bath for 5 minutes. After prehybridization, the slides were washed once in 2×SSC and dehydrated with ethanol as described above.

Hybridization:

Five ug of unlabeled, repeat-enriched Cot-1 blocking DNA [BRL, Gaithersburg, Md. (USA)] and 60 ng of digoxigenin labeled cell line DNA and 20-60 ng of biotin-labeled reference probes (for verification of chromosome identification) were mixed together and 1/10 vol of 3M Na-acetate was added. DNA was precipitated by adding 2 volumes of 100% ethanol followed by centrifugation in a microcentrifuge for 30 minutes at 15,000 RPM. Ethanol was removed and the tubes were allowed to dry until all visible ethanol had evaporated. Ten ul of hybridization buffer consisting of 50% formamide, 10% dextran sulphate and 2×SSC (pH 7) was then added, followed by careful mixing. DNAs in the hybridization buffer were then denatured for 5 minutes at 70° C. followed by a 60 minute renaturation at 37° C. The hybridization mixture was then added to the prehybridized lymphocyte metaphase slides. Hybridization was carried out under a coverslip in a moist chamber for 3-4 days at 37° C.

Immunofluorescent Probe Detection:

The slides were washed three times in 50% formamide/2×SSC, pH 7, twice in 2×SSC and once in 0.1×SSC for 10 minutes each at 45° C. After washing, the slides were immunocytochemically stained at room temperature in three steps (30-45 minutes each). Before the first immunocytochemical staining, the slides were preblocked in 1% BSA/4×SSC for 5 minutes. The first staining step consisted of 2 ug/ml Texas Red-Avidin [Vector Laboratories, Inc., Burlingame, Calif. (USA)] in 1% BSA/4×SSC. The slides were then washed in 4×SSC, 4×SSC/0.1% Triton X-100, 4×SSC, and PN (a mixture of 0.1 M $NaH_2PO_4$ and 0.1 M $Na_2HPO_4$, pH 8, and 0.1% Nonidet P-40) for 10 minutes each and preblocked with PNM (5% Carnation dry milk, 0.02% Na-azide in PN buffer) for 5 minutes. The second antibody incubation consisted of 2 ug/ml FITC-conjugated sheep anti-digoxigenin [Boehringer Mannheim GmBH, Indianapolis, Ind. (USA)] and 5 ug/ml anti-avidin [Vector Laboratories, Burlingame, Calif. (USA)] in PNM followed by three PN washes, 10 minutes each. After the PNM block, the third immunochemical staining was done using rabbit anti-sheep FITC antibody (1:50 dilution) (Vector Laboratories) and 2 ug/ml Texas Red-Avidin in PNM. After three PN washes, nuclei were counterstained with 0.8 uM 4,5-diamino-2-phenylindole (DAPI) in an antifade solution.

Fluorescence Microscopy and Interpretation of Results:

A Nikon fluorescence microscope [Nikon Inc., Garden City, N.Y. (USA)] equipped with a double band pass filter [Chroma Technology, Brattleboro, Vt. (USA)] and a 100× objective was used for simultaneous visualization of the FITC and Texas Red signals. Hybridization of the breast cancer cell line DNAs was seen as a more or less uniform faint green background staining of all metaphase chromosomes with the exception of the Y-chromosome. As the breast cancer cell lines are of course of female origin, they did not contain Y chromosomal DNA. The absence of said green staining of the Y chromosome of the metaphase spread (seen in FIG. 8) is exemplary of the manner in which a cytogenetically significant deletion would be visualized. Using a fluorescence microscope, amplified sequences can be seen as bright green dots or bands along the chromosome arms.

To facilitate the display of the results and to improve the sensitivity of detecting small differences in fluorescence intensity, a digital image analysis system (QUIPS) was used.

QUIPS (an acronym for quantitative image processing system) is an automated image analysis system based on a standard Nikon Microphot SA [Nikon Inc., Garden City, N.Y. (USA)] fluorescence microscope equipped with an automated stage, focus control and filterwheel [Lud1 Electronic Products Ltd., Hawthorne, N.Y. (USA)]. The filterwheel is mounted in the fluorescence excitation path of the microscope for selection of the excitation wavelength. Special filters [Chroma Technology, Brattleboro, Vt. (USA)] in the dichroic block allow excitation of multiple dyes without image registration shift. The microscope has two camera ports, one of which has an intensified CCD camera [Quantex Corp., Sunnyvale, Calif. (USA)] for sensitive high-speed video image display which is used for finding interesting areas on a slide as well as for focusing. The other camera port has a cooled CCD camera [model 200 by Photometrics Ltd., Tucson, Ariz. (USA)] which is used for the actual image acquisition at high resolution and sensitivity.

The cooled CCD camera is interfaced to a SUN 4/330 workstation [SUN Microsystems Inc., Mountain View, Calif. (USA)] through a VME bus. The entire acquisition of multicolor images is controlled using an image processing software package SCIL-Image [Delft Centre for Image Processing, Delft, Netherlands]. Other options for controlling the cameras, stage, focus and filterwheel as well as special programs for the acquisition and display of multicolor images were developed at the Division of Molecular Cytometry [University of California, Medical Center; San Francisco, Calif. (USA)] based on the SCIL-Image package.

To display the results of the comparative hybridization, two or three consecutive images were acquired (DAPI, FITC and Texas Red) and superimposed. The FITC image was displayed after using the thresholding and contrast enhancement options of the SCIL-Image software. Exercising such options reduces the overall chromosomal fluorescence to make amplified sequences more readily visible. For example, using thresholding and contrast stretching, it was possible to enhance the contrast and quantification between the faint green background staining and staining originating from the amplified sequences in the cell lines. Alternatively, to facilitate the detection of deletions, it is possible to increase the overall chromosomal fluorescence and make areas of reduced fluorescence appear darker. The red color was used for reference probes to help in the identification of chromosomes.

After identification of the chromosomes based on the use of reference probes in a dual-color hybridization, a site of amplification was localized by fractional length measurements along the chromosome arm (fractional length=distance of the hybridization signal from the p-telomere divided by the total length of the chromosome). The band location of the signal was then approximated from the fractional length estimate based on the ISCN 1985 idiograms [Harnden and Klinger, *An International System for Cytogenetic Nomenclature*, Karger Ag, Basel, Switzerland (1985)].

Results:

The results from the hybridizations are compiled in Table 2 along with other information known about the cell lines. Amplification at 17q12 (erbB-2 locus) and approximately 8q24 (MYC locus) was seen in lines showing amplification of erbB-2 and MYC whenever the level of amplification was greater than about five- to ten-fold using this CRCC method. In addition, amplification of several megabase wide regions was seen in three cell lines at 17q22-23 and in three lines at 20qter; those amplifications were previously unknown sites of amplification and were not expected from other studies. All lines showing amplification showed amplification at more than one site. Evidence for co-amplification may be clinically important since co-amplification has been observed previously [van de Vijver et al., *Mol. Cell Biol.* 7: 2019-2023 (1987); Saint-Ruf et al., *Oncogene*, 6: 403-406 (1991)], and is sometimes associated with poor prognosis [Borg et al., *Br. J. Cancer*, 63: 136-142 (1991)]. Amplification at 17q22-23 has also been seen using probe DNA from primary tumors.

TABLE 2

Results of Testing Breast Cancer Cell Lines for Amplification

| Cell Line | Origin | Growth rate; -Td | Hormone receptor E/P | Known amplification (level) | Amplification detected by CGH |
|---|---|---|---|---|---|
| BT-474 | Primary Cancer | 48-96 hr | +/- | erbB-2 (13X) | 17q12 (erbB-2), 17q22-23, 20qter |
| SK-BR-3 | Pl. Effusion | ? | ? | erbB-2 (9X) MYC (10X) | 17q12 (erbB-2), 8q21, 8q23-24.1 (MYC), 20qter |
| MDA-MB-361 | Brain met. | <96 hr | -/+ | erbB-2 (4X) | 17q22-23 |
| MCF-7 | Pl. Effusion | <48 hr | +/+ | erbB-2 (none) | 17q22-23, 20qter |
| T-47D | Pl. Effusion | ? | +/+ | erbB-2 (none) | None |
| 600MPE | Pl. Effusion | ? | ? | erbB-2 (none) | None |
| MDA-MB-468 | Pl. Effusion | ? | ? | erbB-2 (none) | None |

EXAMPLE 2

Hybridizations with two different labeled subject DNAs as schematically outlined in FIGS. 6 and 7 were performed. One of the labeled subject DNAs hybridized was a cell line DNA as described in Example 1 and similarly labeled. The other labeled subject DNA was human genomic DNA labeled with biotin-14-dATP.

The protocols were essentially the same as in Example 1 except that no chromosome-specific reference probes were used, and the same amount of the labeled human DNA as the labeled cell line DNA, that is, 60 ng, was hybridized. Of course, reference probes could be added to the hybridization mixture, but they need to be differently labeled to be distinguishable.

The results showed the normal DNA with a red signal and the cell line DNA with a green signal. The green to red ratios were determined along each chromosome. Amplification was indicated by an area where the signal was predominantly green whereas deletions were indicated by more red signals than in other areas of the chromosomes.

Exemplary, CGH results using breast cancer cell line 600MPE DNA and normal human DNA were as follows. As indicated above, the hybridization was performed using 5 ug Cot-1 DNA, 60 ng of digoxigenin labeled 600MPE cell line DNA, and 60 ng of biotinylated normal human genomic DNA. The 600MPE DNA was detected with FITC (green) and the genomic DNA with Texas Red-Avidin (red).

The 600MPE breast cancer cell line, the karyotype for which was published by Smith et al., *JNCI*, 78: 611-615

(1987), contains one normal chromosome 1 and three marker chromosomes with chromosome 1 material in them: t(1q: 13q), 1p(p22) and inv(1)(p36q21). Thus, the cell line is disomic for the p-telomere-p22, trisomic for p22-centromere and tetrasomic for the q-arm of chromosome 1. An idiogram of chromosome 1 showing those different areas is illustrated in FIG. 9.

The comparative genomic hybridizations of this example apparently identified three different regions on chromosome 1 that could be separated according to the intensities of green and red colors. The q-arm of chromosome 1 had the highest intensity of green color (tumor DNA). The region from band p22 to the centromere was the second brightest in green, and the area from the p-telomere to band p22 had the highest intensity of red color (normal DNA). Those hybridization results were consistent with the traditional cytogenetic analyses of that cell line stated immediately above.

However, further studies with CGH, as presented in Example 3, indicated that CGH analysis of Example 2, as well as the published karyotype, were partially in error. The CGH analysis of Example 3 motivated additional confirmatory experiments, as described therein, leading to correction of the original CGH results and the published karyotype.

EXAMPLE 3

Copy Number Karyotypes of Tumor DNA

In the representative experiments of CGH in this example, biotinylated total tumor DNA (cell line and primary tumor DNA) and digoxigenin-labeled normal human genomic DNA are simultaneously hybridized to normal human metaphase spreads in the presence of unlabeled blocking DNA containing high-copy repetitive sequences, specifically unlabeled Cot-1 blocking DNA [BRL, Gaithersburg, Md. (USA)]. The following paragraphs detail the procedures used for the representative CGH experiments of this example.

DNA Labeling:

DNAs used in this example were labeled essentially as shown above in Example 1. DNAs were labeled with biotin-14-dATP or digoxigenin-11-dUTP by nick translation [Rigby et al., supra; Sambrook et al., supra]. The optimal size for double stranded probe fragments after labeling was 600-1000 bp.

Pretreatment of Metaphase Spreads:

Lymphocyte metaphase preparations were denatured, dehydrated and air dried, treated with Proteinase K and dehydrated again as described in Example 1.

Comparative Genomic Hybridization:

Sixty ng of biotinylated test DNA, 60 ng of digoxigenin-labeled normal DNA and 5 µg of unlabeled Cot-1 DNA (BRL) were ethanol precipitated and dissolved in 10 µl of 50% formamide, 10% dextran sulfate, 2×SSC, pH 7. The probe mixture was denatured at 70° C. for 5 minutes, allowed to reanneal at 37° C. for 60 minutes and hybridized to normal male metaphase chromosomes for 3-4 days at 37° C.

Immunofluorescent Probe Detection:

The slides were washed as described above in Example 1, and immunocytochemically stained at room temperature in three thirty-minute steps: (I) 5 µg/ml FITC-Avidin [Vector Laboratories, Inc., Burlingame, Calif. (USA)] and 2 µg/ml anti-digoxigenin-Rhodamine (Boehringer Mannheim GMbH); (II) 5 µg/ml anti-avidin (Vector Laboratories); and (III) 5 µg/ml FITC-avidin. Nuclei were counterstained with 0.8 µM 4,5-diamino-2-phenylindole (DAPI) in antifade solution. A Zeiss fluorescence microscope equipped with a double band pass filter [Chroma Technology, Brattleboro, Vt. (USA)] was used for simultaneous visualization of FITC and rhodamine signals.

Digital Image Analysis System and Fluorescence Ratio Profiles

The QUIPS system essentially a described above in Example 1 was used to analyse quantitatively the fluorescence signals. Fluorescence ratio profiles along the chromosomes were extracted using WOOLZ software package [developed at MRC, Edinburgh, Scotland] as follows: the DAPI image is used to set the morphological boundary of each chromosome by thresholding. The chromosome outline is smoothed by a n number of opening and closing operations, a modified Hilditch skeleton is calculated and taken to represent the medial axis of the chromosome. The DAPI image is expanded outwards in all directions until the intensity field levels off (when background is reached) or begins to rise (due to an adjacent chromosome). The intensity profile of each image along the medial axis and within the expanded DAPI image is then calculated by summing the green and red fluorescence pixel values along the sequence of lines perpendicular to and spaced at unit distance along the medial axis. Modal green and red intensity values corresponding to the expanded DAPI image are taken to represent the background fluorescence and used as the intensity origin.

| Cell Lines: | |
|---|---|
| 5637 | Originated from a human primary bladder carcinoma; obtained from ATCC, catalog # HTB 9 |
| SK-BR-3 | Originated from a human metastatic breast adenocarcinoma, derived from a pleural effusion; obtained from the ATCC, catalog # HTB 30 |
| Colo 205 | Originated from a human colon adenocarcinoma; obtained from the ATCC, catalog # CCL 222 |
| NCI-H508 | Originated from a human cecum adenocarcinoma; obtained from the ATCC, catalog # CCL 253 |
| SW480 | Originated from a humna colon adenocarcinoma; obtained from the ATCC, catalog # CCL 228 |
| SW620 | Originated from a human lymph node metastasis of a colon adenocarcinoma; obtained from the ATCC, catalog # CCL 227 |
| WiDr | Originated from a human colon adenocarcinoma; obtained from the ATCC, catalog # CCL 218 |
| SK-N-MC | Originated from a human neuroblastoma (metastasis to supra-orbital area); obtained from the ATCC, catalog # HTB 10 |
| CaLu3 | Originated from a human lung adenocarcinoma, derived from a pleural effusion; obtained from the ATCC, catalog # HTB 55 |
| CaLu6 | Originated from a human anaplastic carcinoma, probably lung; obtained from the ATCC, catalog # HTB 56 |
| NCI-H69 | Originated from a human small cell lung carcinoma; obtained from the ATCC, catalog # HTB 119 |
| COLO 320HSR | Originated from a human colon adenocarcinoma; obtained from the ATCC, catalog # 220.1 |
| 600 PE | Originated from a human breast carcinoma; obtained from Dr. Helene Smith and Dr. Ling Chen [Geraldine Brush Cancer Research Center, San Francisco, CA (USA)]. This is the same as the 600 MPE cell line described in Examples 1 and 2. |
| BT-20 | Originated from a human breast carcinoma; obtained from ATCC, catalog # HTB 19 |

The following are five fibroblast cell lines with total chromosomal number and X chromosomal number in parentheses, which were obtained from the NIGMS repository [Camden, N.J. (USA)]:

GMO1723 (45,XO)
GMO8399 (46,XX)

GMO4626 (47,XXX)
GMO1415E (48,XXXX)
GMO5009B (49,XXXXX).

Results and Discussion:

Demonstrated herein is CGH's capability of detecting and mapping relative DNA sequence copy number between genomes. A comparison of DNAs from malignant and normal cells permits the generation of a "copy number karyotype" for a tumor, thereby identifying regions of gain or loss of DNA.

Demonstrated is the use of dual color fluorescence in situ hybridization of differently labeled DNAs from a subject tumor genome and a normal human genome to a normal human metaphase spread to map DNA sequence copy number throughout the tumor genome being tested. Regions of gain or loss of DNA sequences, such as deletions, duplications or amplifications, are seen as changes in the ratio of the intensities of the two fluorochromes (used in this representative example) along the target chromosomes. Analysis of tumor cell lines and primary bladder tumors identified 16 different regions of amplification, many in loci not previously known to be amplified. Those results are shown in Table 3 below.

The tumor DNA is detected with the green fluorescing FITC-avidin, and the normal DNA with the red fluorescing rhodamine anti-digoxigenin. The relative amounts of tumor and normal DNA bound at a given chromosomal locus are dependent on the relative abundance of those sequences in the two DNA samples, and can be quantitated by measurement of the ratio of green to red fluorescence. The normal DNA in this example serves as a control for local variations in the ability to hybridize to target chromosomes. Thus, gene amplification or chromosomal duplication in the tumor DNA produces an elevated green-to-red ratio, and deletions or chromosomal loss cause a reduced ratio. The Cot-1 DNA included in the hybridization inhibits binding of the labeled DNAs to the centromeric and heterochromatic regions so those regions are excluded from the analysis.

The fluorescence signals were quantitatively analyzed by means of a digital image analysis system as described above. A software program integrated the green and red fluorescence intensities in strips orthogonal to the chromosomal axis, subtracted local background, and calculated intensity profiles for both colors and the green-to-red ratio along the chromosomes.

The ability of CGH to quantitate changes in sequence copy number that affect an entire chromosome was tested with the above-listed five fibroblast cell lines having 1 to 5 copies of the X chromosome and two copies of each autosome. Hybridization of DNA from the 45,XO cell line (in green) together with normal female DNA (in red) resulted in a uniform green-red staining of the autosomes whereas the X chromosome appeared more red (FIG. 10A). Hybridizations with DNA from cell lines carrying 2, 3, 4 or 5 copies of the X chromosome resulted in an increasingly strong green fluorescence from the X chromosome in relation to the autosomes. The average green-to-red fluorescence ratio of the X chromosome (FIG. 10B), when normalized to the average ratio for the autosomes within the same metaphase spread, increased linearly with the increasing number of X chromosomes [correlation coefficient (r)=0.978]. Thus, CGH can quantitatively distinguish a change of plus or minus one copy of a chromosome at least up to 4 copies.

Experiments showed that CGH could generate a complete copy number karyotype for a near-diploid breast cancer cell line, 600PE. According to the published karyotype for 600PE [Smith et al., *JNCI*, 78: 611 (1987)], 600PE is near-diploid with five marker chromosomes having four copies of the q-arm of chromosome 1, monosomy 16, and deletions of 9p, 11q and 17p. CGH using biotinylated 600PE DNA (in green) and normal digoxigenin-labeled DNA (in red) revealed the following relative copy number changes: gain of 1q and loss of 9p, 16q, 17p and distal 11q. The green-to-red ratio profiles for those aberrant chromosomes are shown in FIG. 11. Only the q-arm of chromosome 16 showed decreased relative copy number suggesting that 16p was not deleted. That observation was subsequently confirmed by fluorescence in situ hybridization (FISH) to 600PE interphase cells using cosmid probes for the p- and q-arms of chromosome 16 [16p and 16q cosmid probes provided by Los Alamos National Laboratory, Los Alamos, N.Mex. (USA)]; two signals per nucleus for the 16p cosmid probe and one for the 16q cosmid probe permitted calibration of a green-to-red ratio of 1.0 as indicating two copies of a sequence.

Thus, if the absolute copy number of any point in the tumor genome is known, relative copy numbers can be converted to actual copy numbers at all loci. The CGH results differed from the originally published karyotype in the region of 16p and proximal 1p. That discrepancy was resolved by locus-specific chromosome-specific painting (FISH) that indicated that the components of one of the marker chromosomes had been misinterpreted by conventional cytogenetic analysis.

CGH with DNAs from two fibroblast cell lines [GMO5877 and GMO1142A from the NIGMS repository] detected small interstitial deletions around the RB1 locus in 13q—del(13) (pter>q14.1::q21.2>qter) and del(13) (pter>q14.1::q22.1>qter). On the basis of the CGH analysis and measurement of the deletion size as a fraction of the length of chromosome 13 (total length 111 Mb), those deletions were estimated to span about 10 and 20 megabases (Mb), respectively. Thus it is possible that CGH can be used to screen DNA samples from solid tumors in order to identify large physical deletions that may uncover recessive mutant tumor suppressor genes.

CGH was evaluated for its ability to detect increased gene copy number with cell lines that contained previously reported amplification of oncogenes. FIG. 12A shows CGH with DNA from a colon cancer cell line COLO 320HSR, known to contain more than a 50-fold amplification of a 300 kb region around the myc oncogene [Kinzku et al., *PNAS* (USA), 83: 1031 (1986)]. The expected high green-to-red ratio at 8q24 corresponding to the location of myc is clear. The height of the peak does not quantitatively reflect the level of amplification because the fluorescent signal spread over a region of the chromosome that is larger than the length of the amplicon. That is apparently a result of the complex organization of the target DNA in the denatured chromosomes.

The eight-fold amplification of the erbB2 oncogene in the SK-BR-3 breast cancer cell line also was detectable with CGH as a hybridization signal at 17q12 (Table 3). High level amplifications such as those also could be detected in single color-hybridizations with the use of only labeled tumor DNA.

Cytogenetic and molecular studies of primary tumors and cell lines often reveal homogeneously staining regions and double minute chromosomes that do not involve known oncogenes [Saint-Ruf et al., *Genes Chrom. Cancer.*, 2: 18 (1990); Bruderlein et al., *Genes Chrom. Cancer*, 2: 63 (1990)]. CGH allows straightforward detection and mapping of such sequences. Table 3 contains a summary of the analysis with CGH of 11 cancer cell lines. Data in Table 3 is based on the visual inspection of a large number of metaphase spreads and on detailed digital image analysis of four to six metaphases for each sample.

TABLE 3

Mapping of amplified sequences in established cancer cell lines and primary tumors by CGH

| Specimen | Origin | Amplif. by CGH* | Cytogenetic evidence of gene amplif.[+] |
|---|---|---|---|
| Cell lines: | | | |
| 5637 | Bladder | 3p25, 6p22 | DM |
| SK-BR-3 | Breast | 8q24 (myc), 8q21, 17q12 (erbB2), 20q13 | |
| Colo 205 | Colorectal | 6p21, 6q24 | |
| NCI-H508 | Colorectal | 14q12-13 | DM |
| SW480 | Colorectal | 8q24 (myc) | DM |
| SW620 | Colorectal | 16q21-23 | HSR |
| WiDr | Colorectal | 8q23-24 (myc) | |
| SK-N-MC | Neuroblastoma | 8q24 (myc) | DM |
| CaLu3 | Small cell lung | 8p12-21, 8qtel, 17q12 (erbB2) | HSR |
| CaLu6 | Small cell lung | 13q32-34 | |
| NCI-H69 | Small cell lung | 2p24 (N-myc), 2p21, 2q21 | |
| Primary tumors: | | | |
| UR140 | Bladder carcinoma | 16q21-22 | |
| UR145 | Bladder carcinoma | 6p22 | |

*The oncogene most likely involved in this amplification is shown in parentheses.
[+]Cytogenetic information based on the ATCC Catalogue of Cell Lines & Hybridomas (1992).
DM = double minute chromosomes,
HSR = homogeneously staining regions.

Sixteen amplified loci were mapped, many at regions of the genome where amplification had not previously been suspected. Thus, a large variety of genes may be amplified during cancer initiation and progression. In five of the 11 cell lines, more than one locus was amplified. Two or three separate loci on the same chromosome were amplified in four cell lines, which suggests a spatial clustering of chromosomal locations that undergo DNA amplification (Table 3 and FIG. 12A).

CGH was also applied to identify and map amplified DNA sequences in uncultured primary bladder tumors. Of the seven tumors tested, two showed evidence of DNA amplification but the loci were not the same (Table 3). Thus, a number of previously unsuspected genomic regions that might contain genes important for cancer progression have been identified by CGH. Further studies will elucidate which of those loci contain novel oncogenes and which represent coincidental, random DNA amplification characteristic of genomic instability.

The detection and mapping of unknown amplified sequences that typically span several hundred kilobases (kb) to a few Mb demonstrated the usefulness of CGH for rapid identification of regions of the genome that may contain oncogenes. Analogously, detection of deletions may facilitate identification of regions that contain tumor suppressor genes.

Further studies are necessary to establish to what extent allelic losses in tumors are caused by physical deletions. In clinical specimens, the detection of small copy number differences is more difficult than with cell lines because of the admixture of DNA from contaminating normal cells and because of intratumor heterogeneity. As indicated above, using PCR to prepare tumor DNA from a small number of tumor cells (as a tumor clonal sub-population) may assist in resolving that problem. Like RFLP, CGH emphasizes the detection of aberrations that are homogeneous in a cell population and averages those that are heterogeneous.

At the current stage of development of CGH, sensitivity is primarily limited by the granularity of the hybridization signals in the metaphase chromosomes. Further improvements in sensitivity will be achieved by optimization of the probe concentration and labeling, and by the averaging of the green-to-red fluorescence ratios from several metaphase spreads.

The descriptions of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to best explain the principles of the invention and its practical application to enable thereby others skilled in the art to best utilize the invention on various embodiments and with various modifications as are suited to the particular use contemplated. It is intended that the scope of the invention be defined by the claims appended hereto. All references cited herein are incorporated by reference.

The invention claimed is:

1. A method of surveying all chromosomes in a human genome for the presence of a copy number variation in one or more unique DNA sequence(s), said method comprising:
   (a) labeling DNA comprising unique sequences from each chromosome from a sample with a label;
   (b) contacting the labeled DNA with a plurality of target nucleic acids comprising unique sequences from each chromosome under conditions that permit non-saturating hybridization of target nucleic acids, wherein either the labeled DNA or the target nucleic acids, or both, have been treated so as to block or remove repetitive sequences, if initially present, without blocking or removing unique sequences; and
   (c) comparing the intensities of the signals from the labeled DNA hybridized to each target nucleic acid to determine the copy number of at least one unique sequence in the hybridized labeled DNA relative to the copy numbers of one or more different unique sequences in the hybridized labeled DNA.

2. The method of claim 1, wherein the labeled DNA comprises total cellular DNA.

3. The method of claim 1, wherein the labeled DNA comprises DNA amplified from total genomic DNA.

4. The method of claim 1, wherein the target nucleic acids comprise a genome or portion thereof.

5. The method of claim 1, wherein the target nucleic acids are immobilized on a substrate.

6. The method of claim 5, wherein the target nucleic acids comprise a metaphase chromosome spread.

7. The method of claim 1, wherein the labeled DNA is contacted with the target nucleic acids in the presence of additional DNA comprising unique sequences from each chromosome, wherein the additional DNA is unlabeled.

8. The method of claim 1, wherein repetitive sequences in the labeled DNA are blocked.

9. The method of claim 1, wherein repetitive sequences in the target nucleic acids are blocked.

10. The method of claim 1, wherein repetitive sequences in the labeled DNA are removed; and unique sequences in the labeled DNA are retained.

11. The method of claim 1, wherein repetitive sequences in the target nucleic acids are removed; and unique sequences in the target nucleic acids are retained.

12. The method according to claim 1, wherein the hybridization is done in situ, the target nucleic acids comprise reference metaphase chromosomes, and the intensities of signals from labeled DNA are compared as a function of position on the metaphase chromosomes.

13. The method of claim 1, wherein the DNA is labeled with a fluorochrome.

14. The method of claim 1, wherein the copy number variation comprises an amplification or a deletion of one or more unique DNA sequences.

15. The method of claim 14, wherein the amplification or deletion comprises an amplification or deletion, respectively, of more than 2 hundred kilobases and less than 20 megabases.

16. The method of claim 1, wherein a chromosomal amplification is detected at a locus on chromosome 1.

17. The method of claim 1, wherein a chromosomal amplification is detected at a locus on chromosome 8.

18. The method of claim 1, wherein a chromosomal amplification is detected at a locus on chromosome 17.

19. The method of claim 1, wherein a chromosomal amplification is detected at a locus on chromosome 20.

20. A method of surveying all chromosomes in a human genome for the presence of a copy number variation in one or more unique DNA sequence(s), said method comprising:
  (a) labeling DNA comprising unique sequences from each chromosome from a sample with a label;
  (b) contacting the labeled DNA with a plurality of target nucleic acids comprising unique sequences from each chromosome under conditions that permit hybridization of target nucleic acids, wherein either the labeled DNA or the target nucleic acids, or both, have been treated so as to block or remove repetitive sequences, if initially present; and
  (c) comparing the intensities of the signals from the labeled DNA hybridized to each target nucleic acid to determine the relative copy numbers of unique sequences in the hybridized labeled DNA.

* * * * *